(12) United States Patent
Montoya et al.

(10) Patent No.: US 9,814,474 B2
(45) Date of Patent: Nov. 14, 2017

(54) RESECTION GUIDES, IMPLANTS AND METHODS

(71) Applicant: NEXTREMITY SOLUTIONS, INC., Warsaw, IN (US)

(72) Inventors: Jorge A. Montoya, Berkeley Heights, NJ (US); John R. Pepper, Cheshire, CT (US); Lon S. Weiner, Rumson, NJ (US); Stuart D. Katchis, Scarsdale, NY (US)

(73) Assignee: Nextremity Solutions, Inc., Warsaw, IN (US)

( * ) Notice: Subject to any disclaimer, the term of this patent is extended or adjusted under 35 U.S.C. 154(b) by 0 days.

(21) Appl. No.: 15/110,342

(22) PCT Filed: Jan. 7, 2015

(86) PCT No.: PCT/US2015/010488
§ 371 (c)(1),
(2) Date: Jul. 7, 2016

(87) PCT Pub. No.: WO2015/105880
PCT Pub. Date: Jul. 16, 2015

(65) Prior Publication Data
US 2016/0324532 A1    Nov. 10, 2016

Related U.S. Application Data

(60) Provisional application No. 61/924,296, filed on Jan. 7, 2014.

(51) Int. Cl.
A61F 5/00        (2006.01)
A61B 17/17       (2006.01)
A61B 17/15       (2006.01)
A61B 17/80       (2006.01)
A61B 17/56       (2006.01)

(52) U.S. Cl.
CPC .......... *A61B 17/1728* (2013.01); *A61B 17/15* (2013.01); *A61B 17/151* (2013.01); *A61B 17/809* (2013.01); *A61B 17/8061* (2013.01); *A61B 17/1775* (2016.11); *A61B 17/8057* (2013.01); *A61B 2017/565* (2013.01)

(58) Field of Classification Search
None
See application file for complete search history.

(56) References Cited

U.S. PATENT DOCUMENTS 5,364,399 A    11/1994   Lowery et al.
5,843,085 A    12/1998   Graser
(Continued)

OTHER PUBLICATIONS

International Search Report and Written Opinion issued in PCT/US2015/010488, dated Jun. 11, 2015.

*Primary Examiner* — Sameh Boles
(74) *Attorney, Agent, or Firm* — Jacque R. Wilson; Wilson Roberts LLP

(57) ABSTRACT

Resection guides, implants and methods are disclosed. A guide may include a plate with a first end opposite a second end and a medial portion extending therebetween. The guide may also include at least one opening in the first end of the plate. The guide may further include at least one hole positioned along a longitudinal axis of the plate near the at least one opening. Surgical methods for using the guide for bone and joint fusions is also disclosed.

9 Claims, 38 Drawing Sheets

(56) References Cited

U.S. PATENT DOCUMENTS

| | | |
|---|---|---|
| 2006/0241608 A1 | 10/2006 | Myerson et al. |
| 2007/0276405 A1 | 11/2007 | Huebner et al. |
| 2011/0106081 A1* | 5/2011 | Graham ............ A61B 17/8023 606/70 |

* cited by examiner

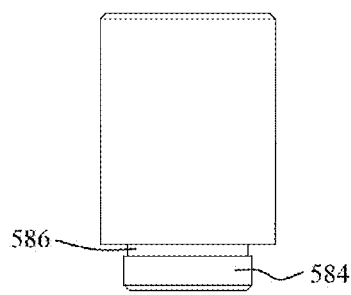
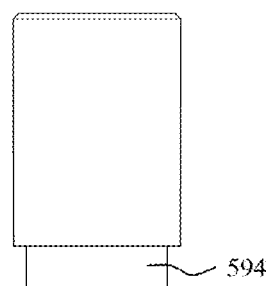
FIG. 24A        FIG. 25A
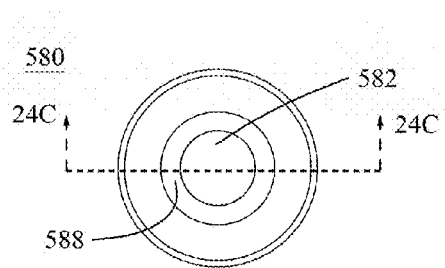
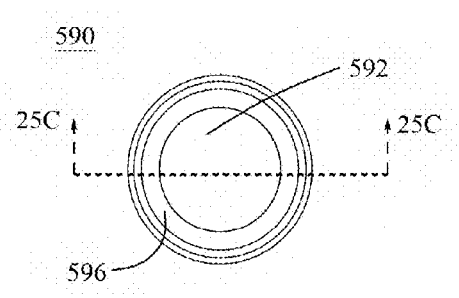
FIG. 24B        FIG. 25B
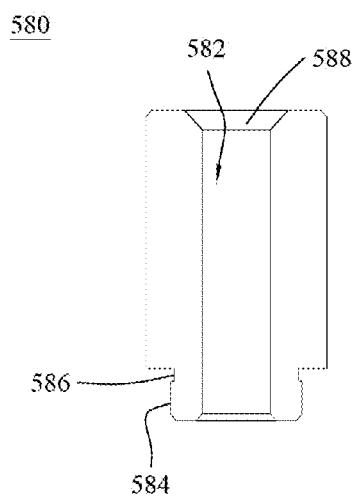
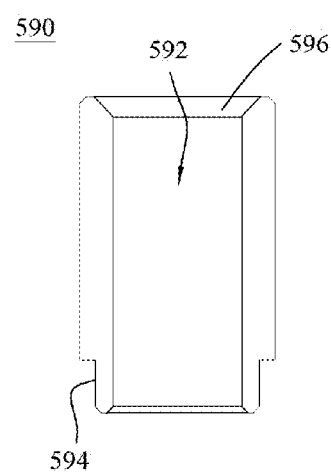
FIG. 24C        FIG. 25C

RESECTION GUIDES, IMPLANTS AND METHODS

CROSS REFERENCE TO RELATED APPLICATION

This application is a U.S. National Phase filing under 35 U.S.C. §371 of International Application No. PCT/US2015/010488, filed Jan. 7, 2015, and published as WO 2015/105880-A1 on Jul. 16, 2015, which claims benefit of priority from U.S. provisional application No. 61/924,296, filed Jan. 7, 2014. The entire contents of each of the prior applications are incorporated herein by reference in their entirety.

FIELD OF THE INVENTION

The present invention relates generally to general surgery, and more particularly to orthopedic surgery. More specifically, but not exclusively, the present invention concerns guides and implants used during surgery for resecting a bone.

BACKGROUND OF THE INVENTION

One such type of bone resection is bunion deformities which are generally found on a person's foot, more specifically they are found on a person's toes. A bunion deformity or hallux abducto valgus deformity results from the big toe deviating laterally toward the patient's smallest toe. Due to the lateral movement of the big toe, the first metatarsal bone angles toward the smaller toes on the patient's foot causing the first metatarsal bone to move out of alignment. Bunions may become irritating and in some cases very painful during walking and other weight bearing activities.

The surgical procedure to fix a bunion deformity is generally a bunionectomy which removes the protruding bone and properly realigns the metatarsal bones to correct the orientation of the foot bones and joints. A number of surgical procedures are available for correcting a bunion deformity. The bunionectomy surgical procedures generally include two stages, first an exostectomy is performed by removing the bunion and then an osteotomy is performed by cutting the metatarsal bone and realigning the two portions to a normal position. Two commonly used surgical procedures are the chevron osteotomy and Reverdin osteotomy. The Reverdin osteotomy includes removal of the medial eminence or bunion and then making two transverse cuts to remove a wedge-shaped portion of bone from the articular surface of the first metatarsal head leaving the lateral cortex intact. The chevron osteotomy includes removal of the bunion and cutting the distal end of the metatarsal bones in a V-shape to enable the bone to be moved back into the correct alignment. After the metatarsal is realigned a small bone screw may be inserted across the cut bone to hold the bone portions in the desired alignment during healing. The Reverdin or chevron osteotomy may be used for mild to moderate hallux abducto valgus deformities. The Reverdin osteotomy changes the angle of the bone segments, and is generally used for more pronounced deformities, while the Chevron moves the segments, but the axes of the bones remain generally parallel. The cuts of the Reverdin osteotomy are typically made free hand without guides, thus surgeons are unable to preplan and execute the precisely angled cuts needed for a Reverdin osteotomy, resulting in Reverdin osteotomies not being performed often, and other techniques and outcomes being performed rather than risk the difficult to visualize Reverdin osteotomy. The V-shaped cuts of the Reverdin or chevron osteotomy near the metatarsal head allow the portions of the metatarsal bones to be realigned without compromising the joint.

SUMMARY OF THE INVENTION

Aspects of the present invention provide guides, implants, and methods for correcting a bone deformity, for example, a bunion.

In one aspect, provided herein is a guide including a plate with a first end opposite a second end and a medial portion extending therebetween. The guide may also include at least one opening in the first end of the plate. Further, the guide may include at least one hole positioned along a longitudinal axis of the plate near the at least one opening.

In another aspect, provided herein is a surgical method for correcting a bone deformity including removing a piece of bone from a bone and aligning a guide on the bone over an area of bone where the piece of bone was removed. The method may also include inserting at least one temporary fixation device into an opening in the guide. In addition, the method may include drilling at least one opening into the bone through at least one drill opening in the guide. The method may further include removing the at least one temporary fixation device to remove the guide from the bone. The method may also include cutting the bone along the first cut line and at least one second cut line. Further, the method may include inserting at least one engagement portion of an implant into the at least one opening in the bone. Finally, the method may include inserting at least one fastener through the implant to secure the implant to the bone.

In yet another aspect, provided herein is a surgical method for bone or joint fusions including aligning a guide on at least one bone and drilling at least one opening into the at least one bone through at least one drill opening in the guide. The method may also include providing a templating means for an osteotomy and cutting the bone along a first cut line and at least one second cut line. The method may further include inserting at least one engagement portion of an implant into the at least one opening in the bone. Finally, the method may include inserting at least one fastener through the implant to secure the implant to the bone.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention.

FIG. 24A is a side view of a screw sleeve for a guide, in accordance with an aspect of the present invention;

FIG. 24B is a top view of the screw sleeve of FIG. 24A, in accordance with an aspect of the present invention;

FIG. 24C is a side cross-sectional view of the screw sleeve of FIG. 24A taken along line 24C-24C in FIG. 24B, in accordance with an aspect of the present invention;

FIG. 25A is a side view of a screw sleeve for a guide, in accordance with an aspect of the present invention;

FIG. 25B is a top view of the screw sleeve of FIG. 25A, in accordance with an aspect of the present invention;

FIG. 25C is a side cross-sectional view of the screw sleeve of FIG. 25A taken along line 25C-25C in FIG. 25B, in accordance with an aspect of the present invention;

DETAILED DESCRIPTION FOR CARRYING OUT THE INVENTION

Generally stated, disclosed herein are a number of embodiments of guides, devices, and implants used during surgery to correct a bone deformity. Also disclosed herein are surgical methods for using the guides, devices, and implants.

In this detailed description and the following claims, the words proximal, distal, anterior, posterior, medial, lateral, superior, inferior, dorsal and plantar are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom or sole of the foot.

Similarly, positions or directions may be used herein with reference to anatomical structures or surfaces. For example, as the current devices, instrumentation and methods are described herein with reference to use with the bones of the foot, ankle and lower leg, the bones may be used to describe the surfaces, positions, directions or orientations of the devices, instrumentation and methods. Further, the devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices, instrumentation and methods, and the aspects, components, features and the like thereof, described herein with respect to the right foot may be mirrored so that they likewise function with the left foot. Further, the devices, instrumentation and methods, and the aspects, components, features and the like thereof, disclosed herein are described with respect to the big toe or hallux for brevity purposes, but it should be understood that the devices, instrumentation, and methods may be used with other bones of the foot having similar structures.

Figure 1:
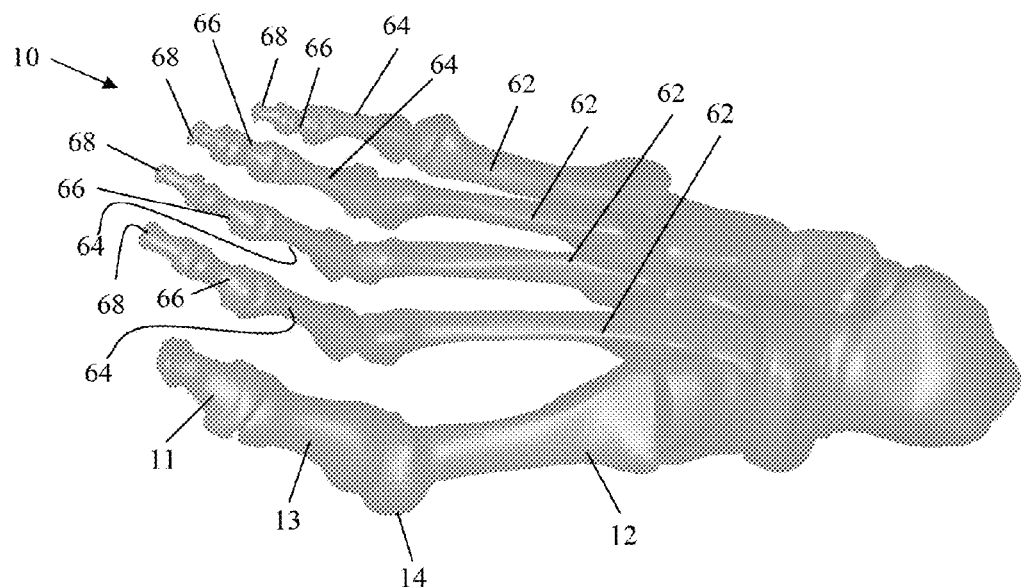
FIG. 1 is a perspective view of the bones of a right foot with a hallux valgus deformity, in accordance with an aspect of the present invention.
Figure 2:
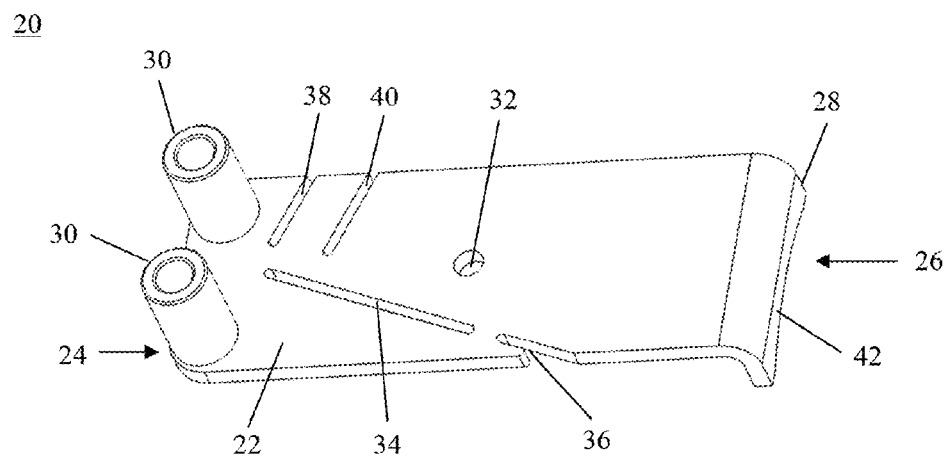
FIG. 2 is a perspective view of one embodiment of a guide, in accordance with an aspect of the present invention.

Referring to the drawings, wherein like reference numerals are used to indicate like or analogous components throughout the several views, and with particular reference to FIG. 1, in one example, the bones of a foot 10 with a hallux valgus or bunion deformity 14 of the metatarsal bone 12 is shown. The terms "bone deformity," "hallux valgus deformity," "bunion deformity" and "bunion" may be used interchangeably herein as they essentially describe the same type of deformity. In FIG. 1, the foot 10 is a right foot, but all devices, guides, implants and methods may be used likewise on the left foot, as well as on other bones containing deformities. The bone deformity 14 may be removed from the metatarsal bone 12 using a bone saw (not shown) or another known method for removing a segment of bone. After the bunion 14 is removed the metatarsal bone 12 and the distal and proximal phalanges 11, 13 may be realigned.

Referring now to FIGS. 2-7, one embodiment of a guide 20 is shown. The guide 20 includes a plate 22 with a first end 24 and a second end 26. The first end 24 may be the distal end of the plate 22 and the second end 26 may be the proximal end of the plate 22. The second end 26 may include a first member 28 extending out from the second end 26 in an inferior direction. The guide 20 may also include at least one opening 30, for example, two screw sleeves are shown, near the first end 24. In addition, the guide 20 may include at least one aperture 32 in a medial portion of the plate 22. The plate 22 may further include a first reference surface 34 extending from a point near the first end 24 to a point near the second end 26 and angled relative to the longitudinal axis. In addition, the plate 22 may include a notch 36 on a side of the plate 22 near the second end 26. The notch 36 may also be aligned with the first reference surface 34. The plate 22 may further include at least one second reference surface 38, 40. As shown, the plate 22 may include, for example, a second reference surface 38 and a third reference surface 40 both extending into the plate 22, for example, from a side of the plate 22 opposite the first reference surface 34. The second reference surface 38 may be relatively parallel to the third reference surface 40 from a top view of the plate 22.

Figure 3:
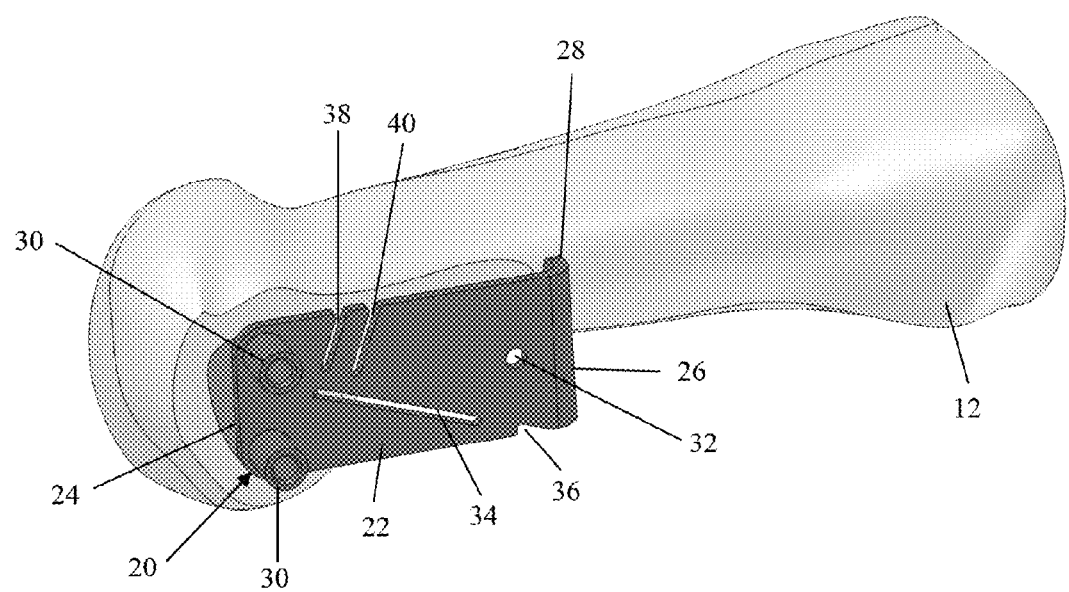
FIG. 3 is a perspective view of a first metatarsal bone with a guide, in accordance with an aspect of the present invention.

As shown in FIG. 3, the plate 22 may be angled relative to the first member 28 enabling alignment of the first reference surface 34, second reference surface 38, and third reference surface 40 in a desired orientation for performing the osteotomy to remove a segment of the metatarsal bone 12. The size of the first member 28 determines the angle of the plate 22. The angle of the plate 22 may range from, for example, about 20 degrees to about 110 degrees. The first member 28 of the guide 20 may include a curved segment 42 corresponding to the curve of the bone 12 to assist in the alignment of the guide 20 with the bone 12.

Figure 4:
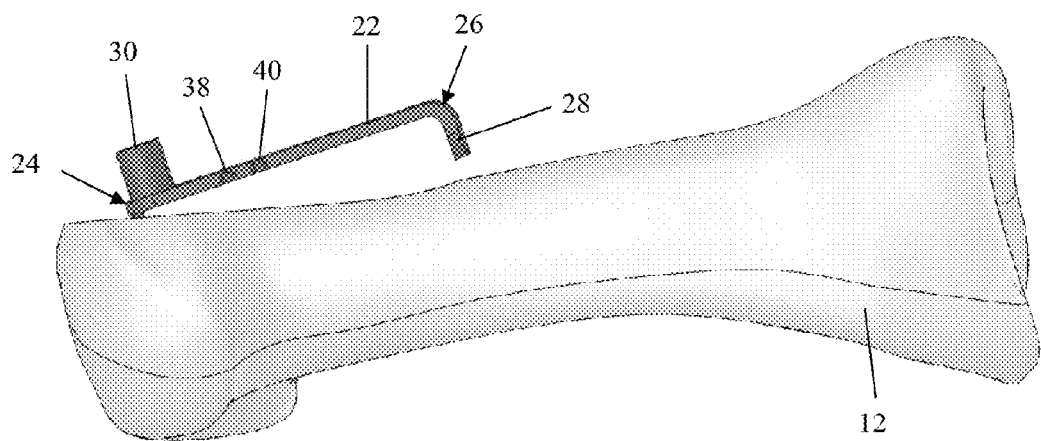
FIG. 4 is a plantar view of the first metatarsal bone and guide of FIG. 3, in accordance with an aspect of the present invention.
Figure 5:
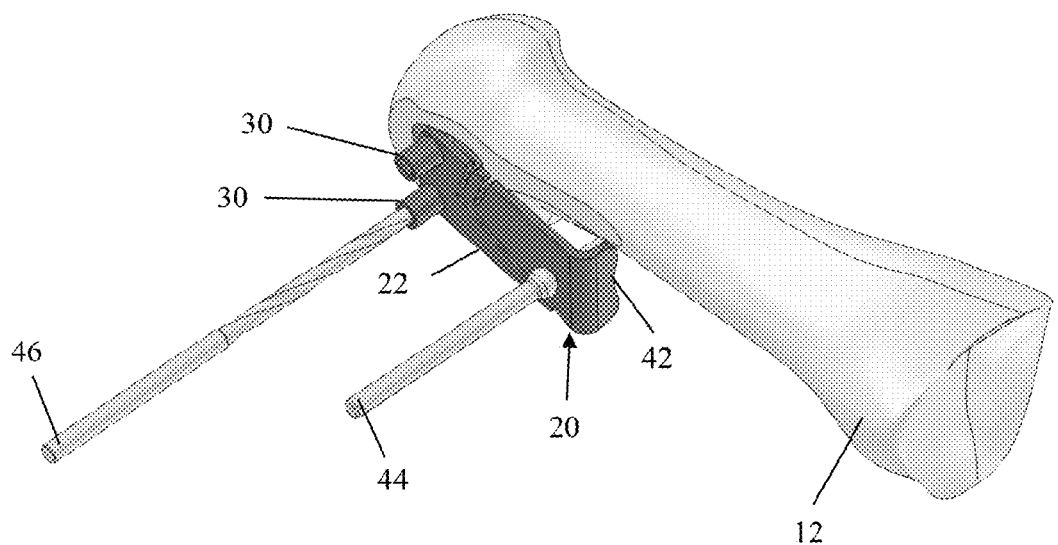
FIG. 5 is a proximal perspective view of the first metatarsal bone and guide of FIG. 3 with a fixation device and drill bit inserted into the guide, in accordance with an aspect of the present invention.
Figure 6:
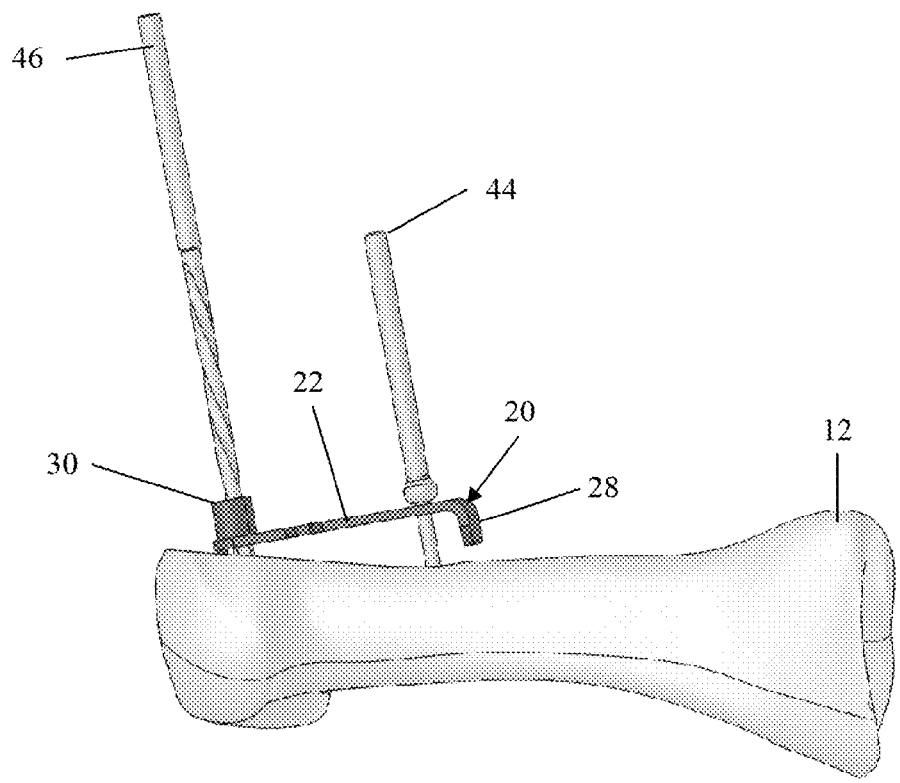
FIG. 6 is a plantar view of the first metatarsal bone shown in FIG. 5, in accordance with an aspect of the present invention.

Referring now to FIGS. 3-7, the method for using the guide 20 to perform an osteotomy, for example, a distal osteotomy, is shown. As seen in FIGS. 3 and 4, the guide 20 is aligned with the bone 12 after the bone deformity 14 has been removed. Once the guide 20 is aligned with the bone 12, a temporary fixation device 44 may be inserted into the bone 12 through the aperture 32. The temporary fixation device 44 holds the guide 20 to the bone 12. The temporary fixation device 44 may be, for example, a pin, wire, olive wire or the like. After the guide 20 is held to the metatarsal bone 12, a drill 46 may be inserted through the openings 30 to drill holes 48 into the metatarsal bone 12, as shown in FIGS. 5 and 6. The holes 48 may be used for holding the guide 20 to the metatarsal bone 12 while the bone 12 is cut. In addition, the holes 46 may be used for inserting the implant 100.

Figure 7:
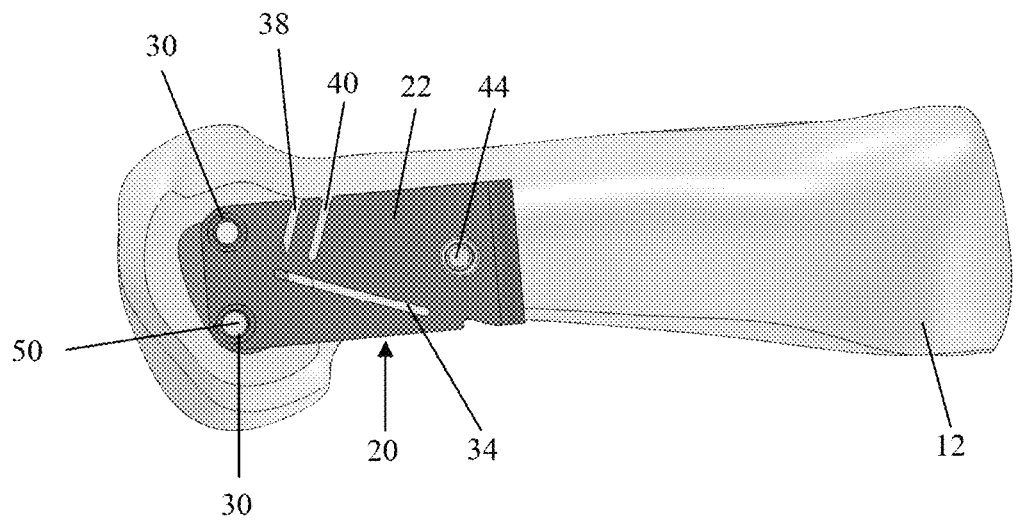
FIG. 7 is a medial view of the first metatarsal bone and guide of FIG. 3 showing the guide temporarily fixed to the bone, in accordance with an aspect of the present invention.

Referring now to FIG. 7, temporary fixation devices 50 may optionally be inserted through the openings 30 and into the drill holes 48 to hold the guide 20 to the metatarsal bone 12 while the metatarsal bone 12 is cut. In one embodiment, three cuts may be made, a cut in the second reference surface 38 and a cut in the third reference surface 40 to create a desired V-shape, for example, a wedge shape, and a cut in the first reference surface 34 to engage the other cuts and create two segments of the metatarsal bone 12. The first reference surface 34 may allow for a cut into the metatarsal bone 12 from the plantar side of the foot 10 to engage the cuts made using the second and third reference surfaces 38, 40. The second reference surface 38 and third reference surface 40 may start on the dorsal side of the metatarsal bone 12 and pass into the middle of the metatarsal bone 12. The second and third reference surfaces 38, 40 may also be angled towards each other to create the desired size and shape cutout of the metatarsal bone 12.

Figure 8:
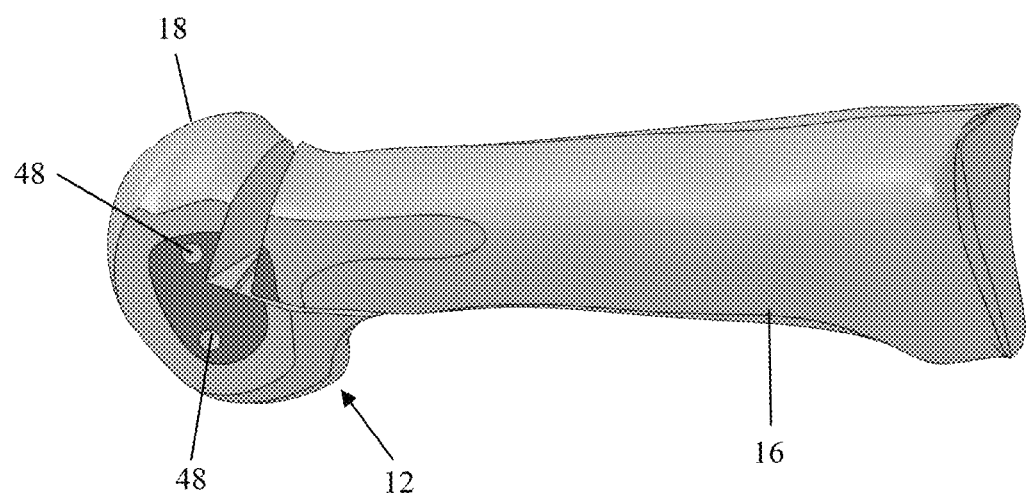
FIG. 8 is a medial view of the first metatarsal bone of FIG. 3 after a segment of bone is removed, in accordance with an aspect of the present invention.
Figure 9:
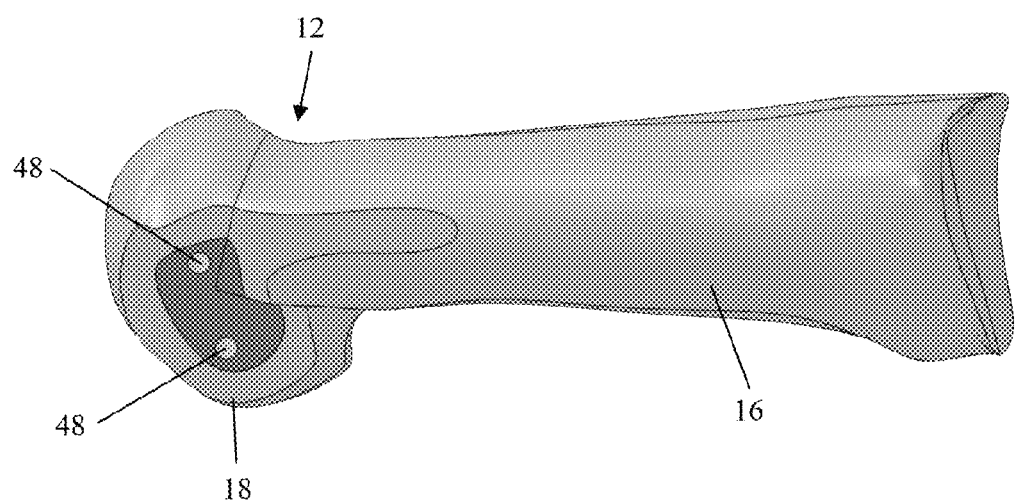
FIG. 9 is a medial view of the first metatarsal bone of FIG. 8 after reduction of the segments of the bone, in accordance with an aspect of the present invention.

FIG. 8 shows the metatarsal bone 12 after the three cuts have been made creating a first bone segment 16 and a second bone segment 18. The first bone segment 16 is the proximal end of the metatarsal bone 12 and the second bone segment 18 is the distal end of the metatarsal bone 12. By removing a medial segment of the metatarsal bone 12, the joint surfaces are left intact thereby not altering the joints of the foot 10. Once the cuts are completed the first bone segment 16 and second bone segment 18 may be reduced to align the cut surfaces and close the opening created by the cuts. After the first bone segment 16 and second bone segment 18 are aligned, as shown in FIG. 9, an implant 100 may be inserted into the second bone segment 18 and attached to the first bone segment 16 to hold the metatarsal bone 12 in place during the healing process.

Figure 10:
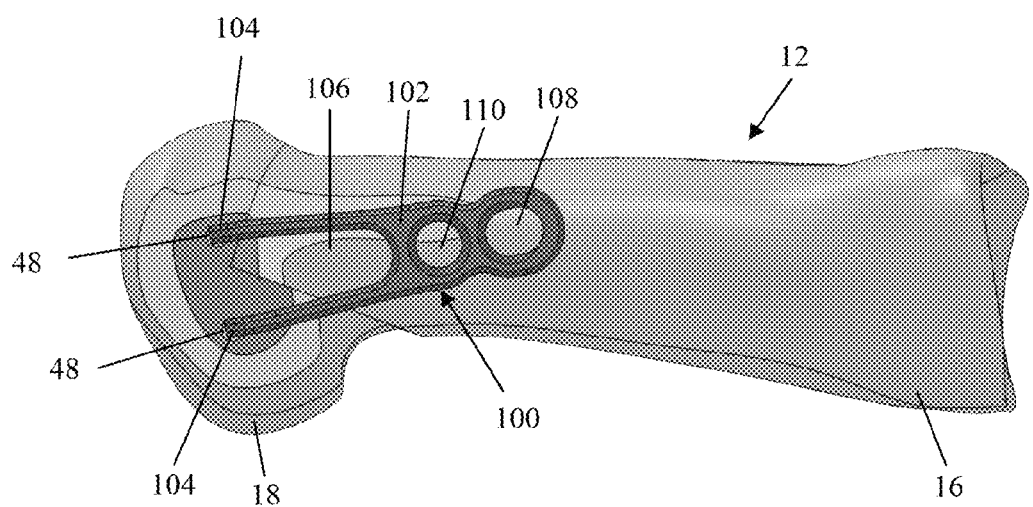
FIG. 10 is a medial view of the first metatarsal bone of FIG. 3 with an implant inserted over the cuts, in accordance with an aspect of the present invention.
Figure 32:
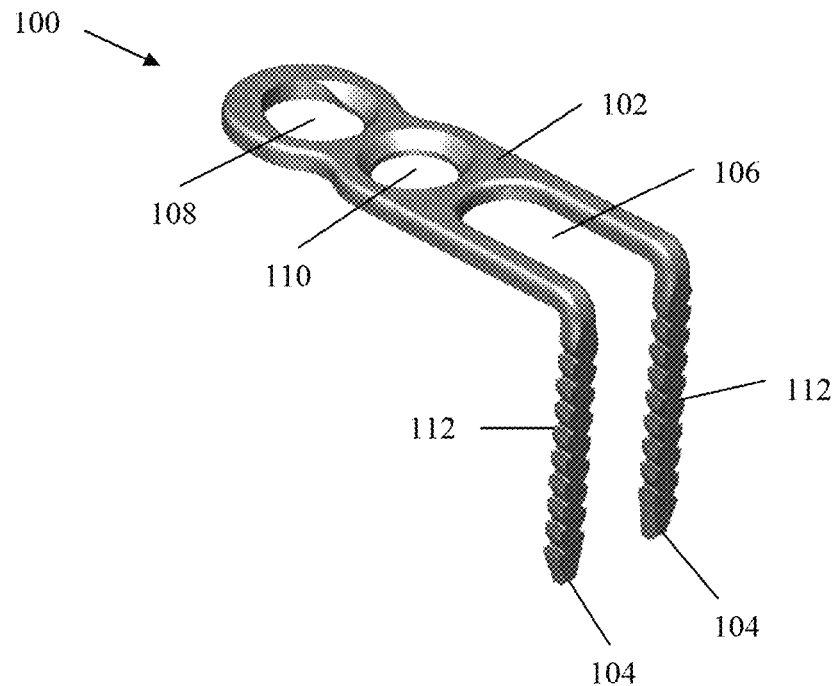
FIG. 32 is a perspective view of an implant, in accordance with an aspect of the present invention.

Referring now to FIGS. 10 and 32, the implant 100 may include a body member 102 with at least one engagement portion 104 extending relatively perpendicular from the body member 102. As shown in one embodiment, the implant 100 may include, for example, two engagement portions 104. The body member 102 may also include at least one opening 106 in the distal portion of the implant 100 defined by opposing engagement portions 104. The opening 106 may enable visualization of the first and second bone segments 16, 18 when the implant 100 is inserted into the patient. In addition, the body member 102 may include at least one slot 108, for example a compression slot, allowing for movement of the first bone segment 16 relative to the second bone segment 18 as a first bone fastener (not shown) is inserted into the compression slot 108. The compression slot 108 is configured to facilitate the application of a compressive force across the osteotomy when the bone fastener is tightened. The body member 102 may also include an aperture 110 for inserting a second fastener (not shown) after the first fastener has completed the desired compression of the first and second bone segments 16, 18. The at least one engagement portion 104 may include engagement members 112 (See FIG. 32) to assist in holding the engagement portions 104 in the holes 48 in the second bone segment 18. The engagement members 112 may be, for example, ridges, barbs, spikes, and teeth-like or tine-like structures. The implants 100 may come in a variety of sizes to correspond to the different size metatarsal bones 12 in people.

As shown in FIG. 10, the engagement portions 104 of the implant 100 may be inserted into the holes 48 in the second bone segment 18 of the metatarsal bone 12. Once the engagement portions 104 are inserted into holes 48, the opening 106 aligns over the cuts in the metatarsal bone 12 enabling visualization of the alignment of the first and second bone segments 16, 18. In addition, the compression slot 108 and aperture 110 are aligned over the first bone segment 16. The method of fixing the implant 100 to the metatarsal bone 12 will be discussed in greater detail below.

Figure 11:
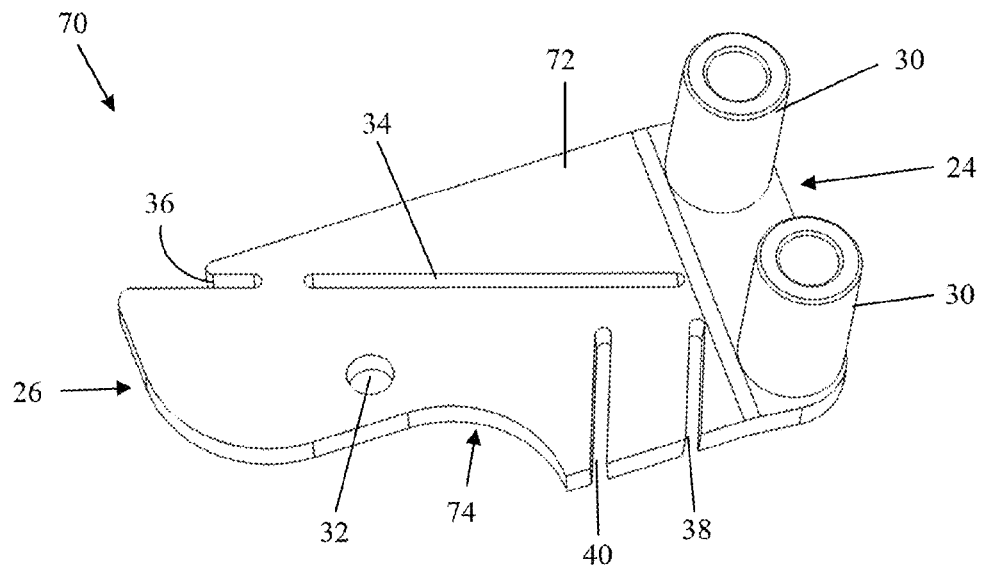
FIG. 11 is a perspective view of one embodiment of a guide, in accordance with an aspect of the present invention.
Figure 12:
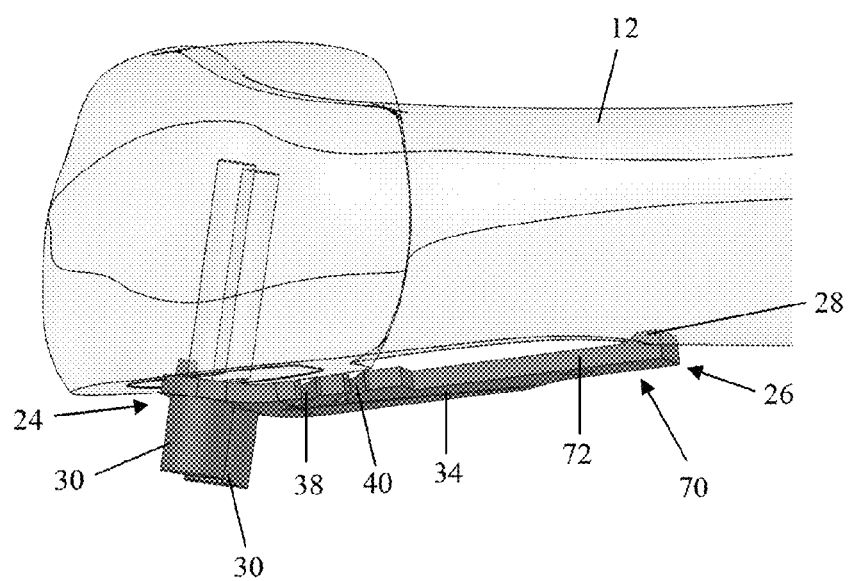
FIG. 12 is a dorsal view of a first metatarsal bone with the guide of FIG. 11 aligned on the bone, in accordance with an aspect of the present invention.

Referring now to FIGS. 11 and 12, another embodiment of the guide 70 is shown. The guide 70 shown in FIGS. 11 and 12 is similar to the type described above with reference to FIGS. 2-7, however the first member 28 of the guide 70 is smaller and the plate 72 includes an angled segment at the first end 24 where the openings 30 are placed and a cutout 74 at the second end 26. The size of the first member 28 enables the surgeon to determine the size and alignment of the bone cuts using reference surfaces 34, 38, 40.

Figure 13:
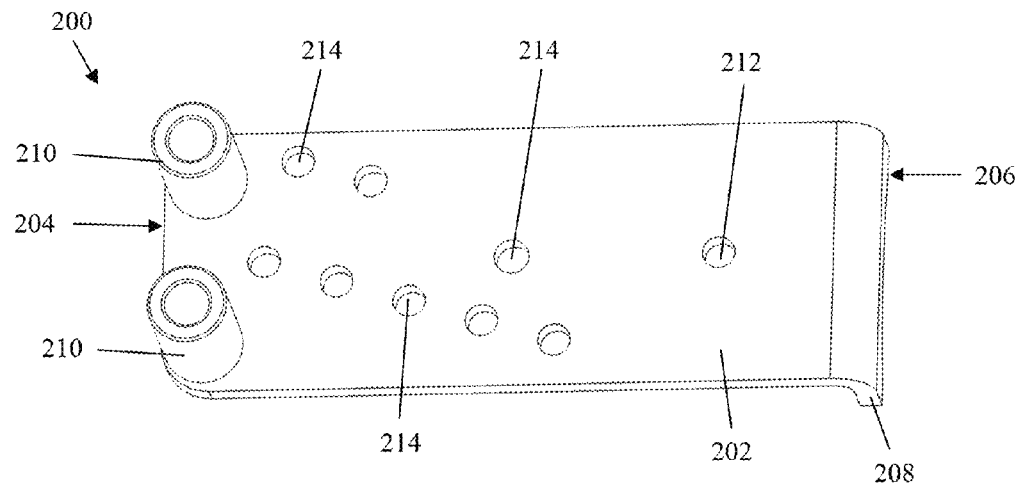
FIG. 13 is a top perspective view of an embodiment of a guide, in accordance with an aspect of the present invention.
Figure 14:
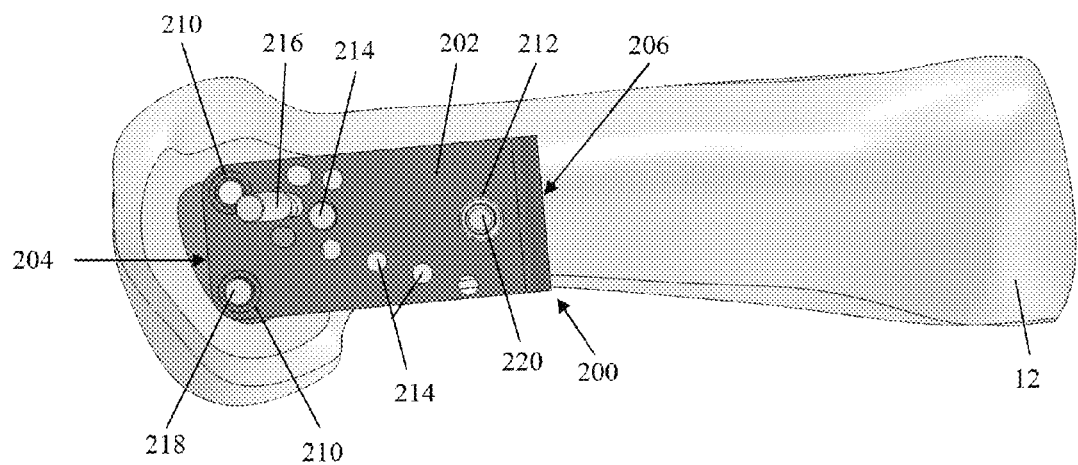
FIG. 14 is a medial view of a first metatarsal bone with the guide of FIG. 13, in accordance with an aspect of the present invention.
Figure 15:
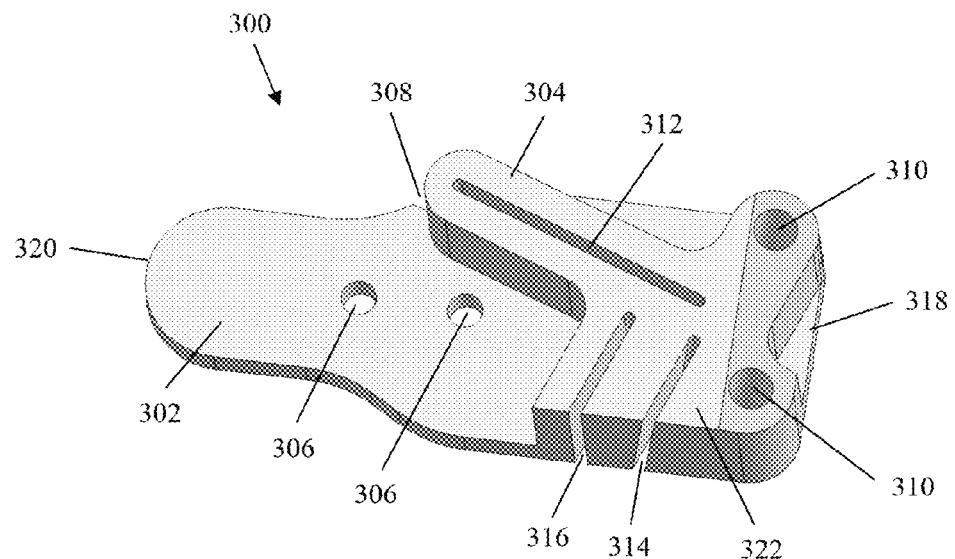
FIG. 15 is a top perspective view of another bone cutting guide, in accordance with an aspect of the present invention.

An embodiment of guide 200 is shown in FIGS. 13 and 14. The guide 200 includes a base 202 with a first end 204 and a second end 206. The guide 200 may also include an extension member 208 at the second end 206 extending relatively perpendicular from the base 202 to engage the metatarsal 12. The base 202 may include at least one drill hole 210 at the first end 204 of the guide 200 and at least one aperture 212 at the second end 206 of the guide 200. As shown in FIGS. 13 and 14, the depicted embodiment of guide 200 has two drill holes 210 and one aperture 212. In addition, the base 202 of the guide 200 may also include a plurality of openings 214 dispersed along the length of bone 202.

As shown in FIG. 14, the aperture 212 of the guide 200 may be used to temporarily fix the guide 200 to the metatarsal bone 12 with a temporary fixation device 220. The openings 210 may be used to insert a drill 216 into the metatarsal bone 12 to drill holes 48 (see FIGS. 8 and 9) for the implant 100. In addition to temporary fixation device 220 in the second end 206 of the guide 200, temporary fixation devices 218 may be inserted into the drill holes 48 through openings 210 in the first end 204 of the guide 200. The temporary fixation devices 218, 220 may hold the guide 200 to the metatarsal bone 12 while a plurality of guide holes (not shown) are drilled through the plurality of openings 214. The openings 214 may be along the base 202 between the first end 204 and the second end 206. The openings 214 may be placed where the cuts of the osteotomy will occur to create a guide for the surgeon when cutting the metatarsal bone 12. Once the surgeon creates drill marks for the openings 214, the temporary fixation devices 218, 220 may be removed and the guide 200 may be removed from the patient. Then the physician may cut the metatarsal bone 12 by cutting along the drill marks created through the openings 214. Finally, the implant 100 may be aligned and secured to the metatarsal 12 as discussed in greater detail below.

Referring now to FIGS. 15-20, another guide embodiment 300 is shown. The guide 300 may include a plate 302 and a guide body 304 extending out from the plate 302. The plate 302 may include a first end 318 and a second end 320. The plate 302 may also include at least one aperture 306 for inserting at least one temporary fixation device (not shown) and a notch 308. In addition, the plate 302 may include openings 310 near the second end 320 of the plate 302 and extending through the guide body 304. The plate 302 may further include a first reference surface 312, a second reference surface 314, and a third reference surface 316 extending from the plate 302 into and through the guide body 304.

Figure 17:
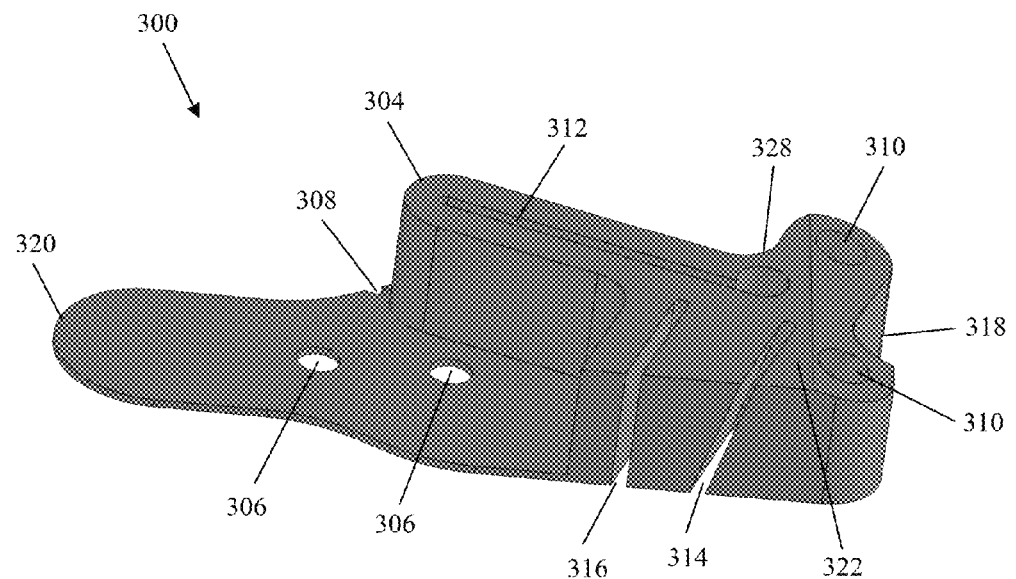
FIG. 17 is a lateral perspective view of the bone cutting guide of FIG. 15, in accordance with an aspect of the present invention.
Figure 18:
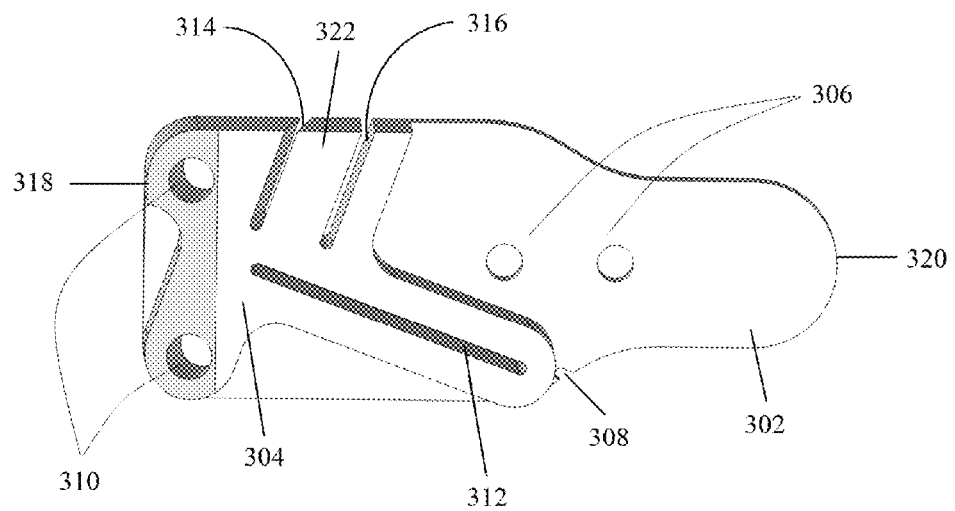
FIG. 18 is a top view of the bone cutting guide of FIG. 15, in accordance with an aspect of the present invention.
Figure 19:
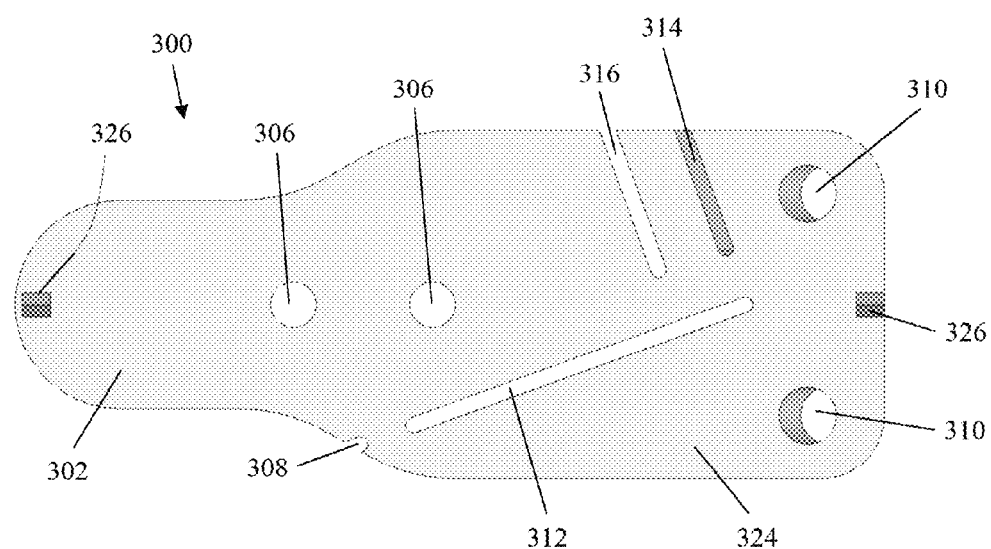
FIG. 19 is a bottom view of the bone cutting guide of FIG. 15, in accordance with an aspect of the present invention.
Figure 20:
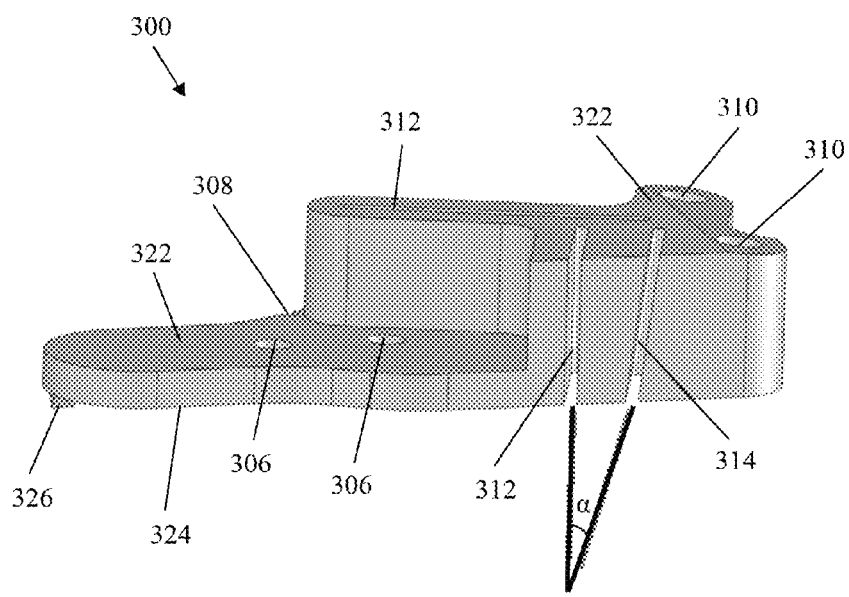
FIG. 20 is a lateral view of the bone cutting guide of FIG. 15 showing the angles of the two reference surfaces, in accordance with an aspect of the present invention.

As shown in FIGS. 18 and 19, the first reference surface 312 may extend from a position near the notch 308 to a position near the openings 310. The notch 308 and the first reference surface 312 may be aligned. The first reference surface 312 may also be angled relative to the longitudinal axis of the guide 300. The second reference surface 314 may extend from an exterior side surface of the guide 300 and into the plate 302 and guide body 304 toward the first reference surface 312. The third reference surface 316 may also extend from an exterior side surface of the guide 300 and into the plate 302 and guide body 304 toward the first reference surface 312. The second reference surface 314 and third reference surface 316 may be relatively parallel to each other on the top surface 322 and bottom surface 324 of the guide 300. In addition, the second reference surface 314 and third reference surface 316 may be angled from the top surface 322 of the guide 300 to the bottom surface 324 of the guide 300. As illustrated in FIGS. 17 and 20, the second and third reference surfaces 314, 316 are angled towards each other as they extend from the top surface 322 to the bottom surface 324 of the guide 300. The angle of the second and third reference surfaces 314, 316 allows a wedge shaped segment of bone to be removed from the metatarsal bone 12. As shown in FIG. 20, the second and third reference surfaces 314, 316 of the guide 300 of FIG. 20 create a bone segment with an angle α. The angle α may range from, for example, 0 degrees to 50 degrees.

Figure 16:
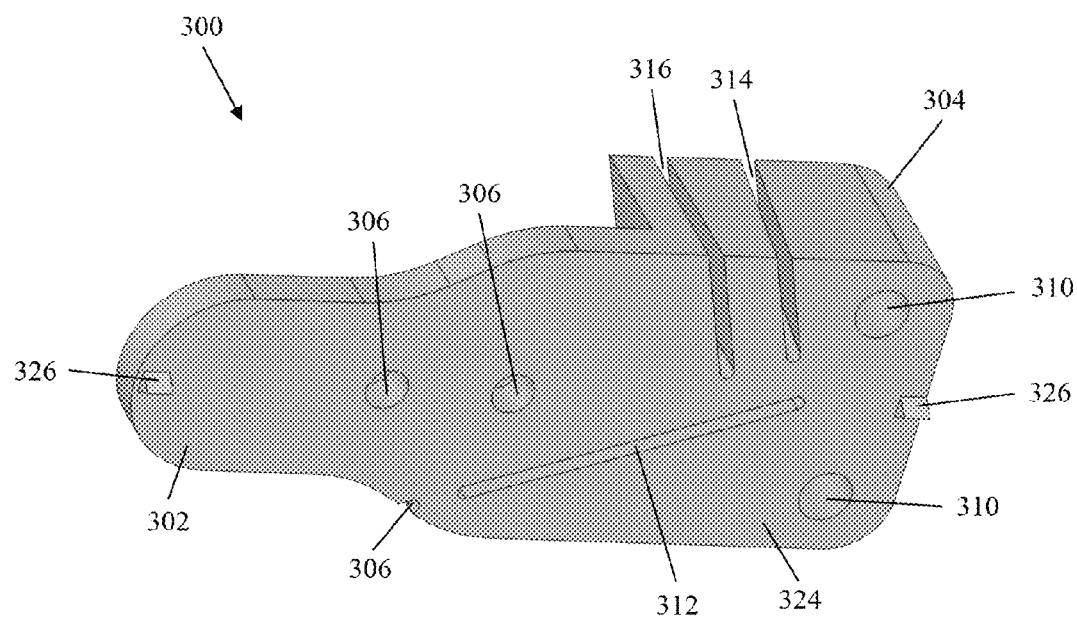
FIG. 16 is a bottom perspective view of the bone cutting guide of FIG. 15, in accordance with an aspect of the present invention.

Referring now to FIGS. 16, 19 and 20, the guide 300 may also include at least one protrusion 326 extending out from the bottom surface 324 of the guide 300. The at least one protrusion 326 may assist in providing stability to the guide 300 when it is aligned and secured to the metatarsal bone 12 for performing an osteotomy. In one embodiment, as depicted, the guide 300 includes two protrusions 326. The guide 300 may also include an apex hole 328 in the first reference surface 312, as shown in FIG. 17. The hole 328 may be used to drill an opening in the metatarsal bone 12. An opening drilled through the hole 328 may be used to assist in inserting a bone saw into the first reference surface 312.

Figure 21:
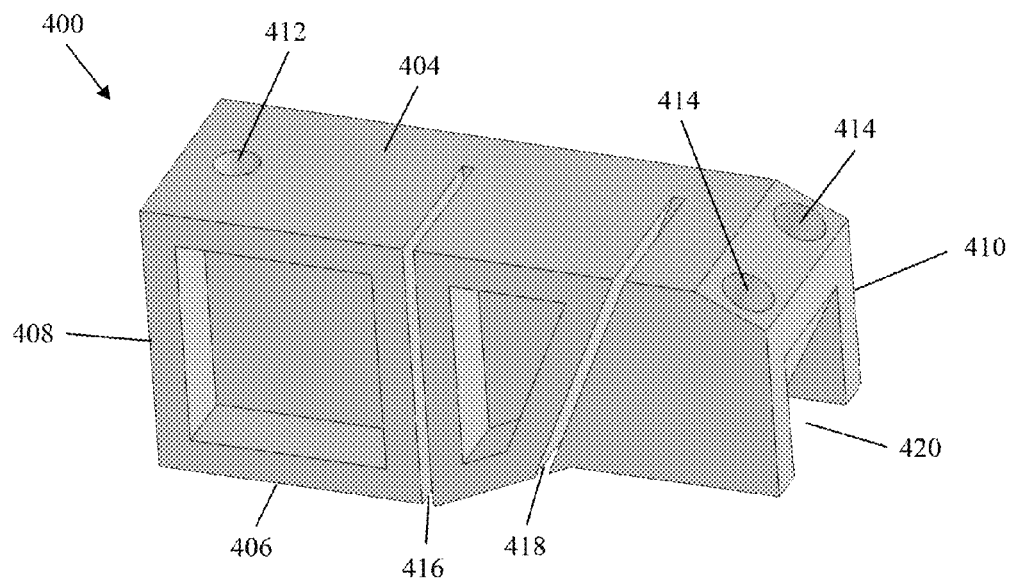
FIG. 21 is a perspective view of an embodiment of a bone cutting guide, in accordance with an aspect of the present invention.
Figure 22A:
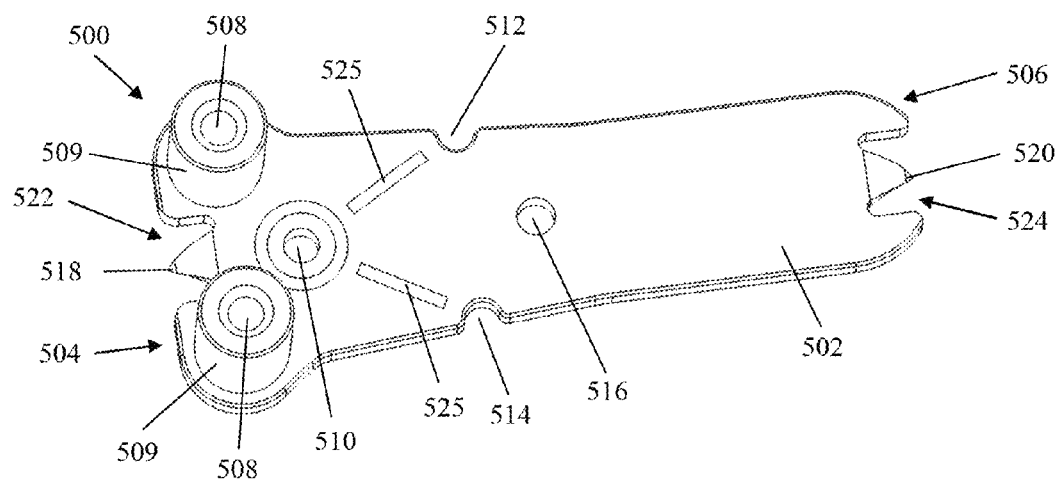
FIG. 22A is a top perspective view of another embodiment of a guide, in accordance with an aspect of the present invention.
Figure 22B:
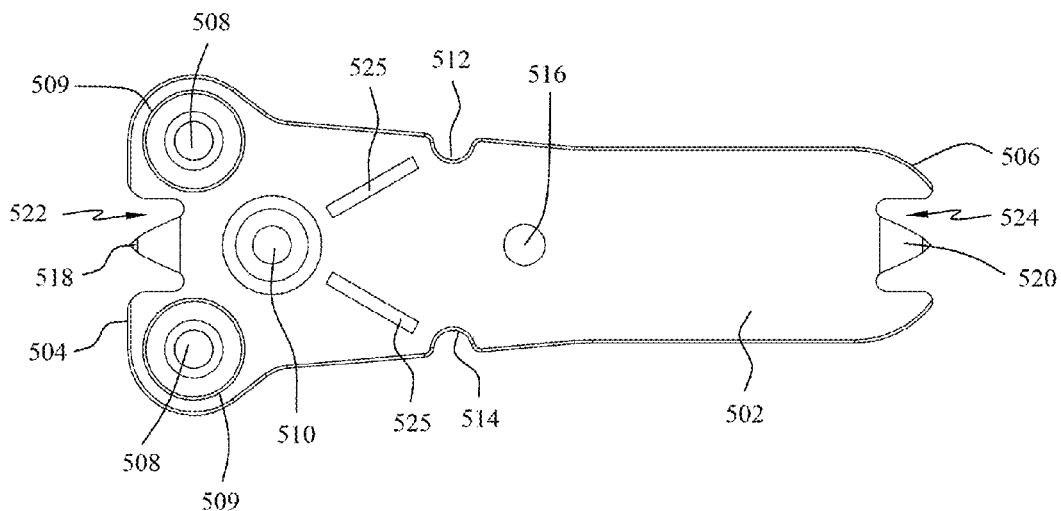
FIG. 22B is a top view of the guide of FIG. 22A, in accordance with an aspect of the present invention.
Figure 22C:
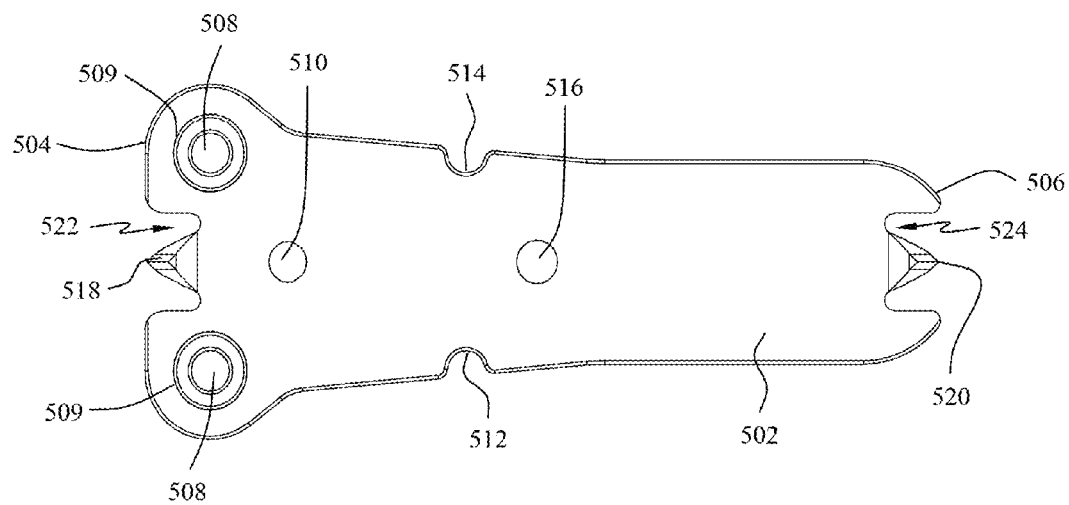
FIG. 22C is a bottom view of the guide of FIG. 22A, in accordance with an aspect of the present invention.
Figure 22D:
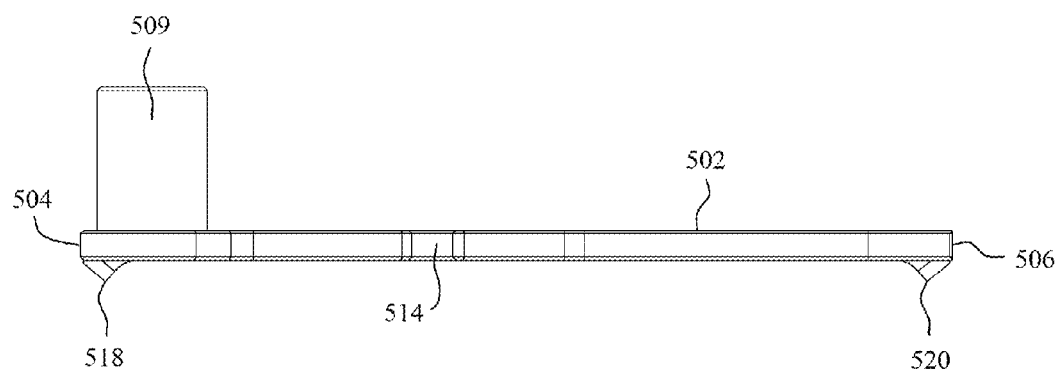
FIG. 22D is a side view of the guide of FIG. 22A, in accordance with an aspect of the present invention.
Figure 22E:
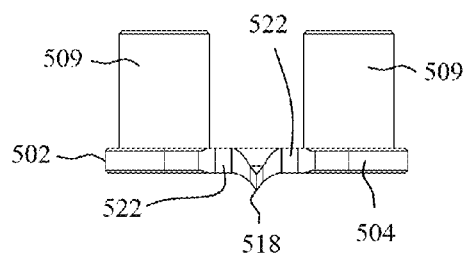
FIG. 22E is a first end view of the guide of FIG. 22A, in accordance with an aspect of the present invention.
Figure 22F:
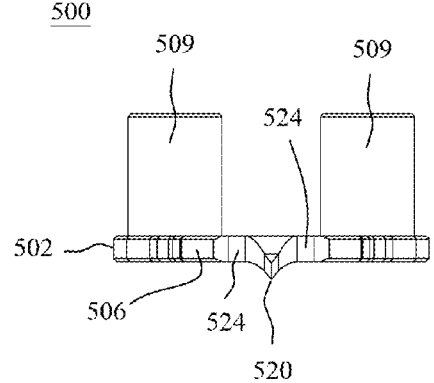
FIG. 22F is a second end view of the guide of FIG. 22A, in accordance with an aspect of the present invention.

Referring now to FIG. 21, another embodiment of guide 400 is shown. The guide 400 may include a base 402 with a top surface 404, a bottom surface 406, and at least four sides connecting the top and bottom surfaces 404, 406. Two of the sides of the guide 400 may be a first end 408 and a second end 410 opposite the first end 408. The guide 400 may also include an aperture 412 near the first end 408 and at least one opening 414 near the second end 410. The aperture 412 may be used for inserting a temporary fixation device, not shown, to hold the guide 400 to a patient's metatarsal bone 12. The openings 414 may be used for drilling holes (not shown) in the metatarsal bone 12 for insertion of the implant 100 and may be, for example, straight or angled. In addition, the guide 400 may include a first reference surface 416 and a second reference surface 418. The first reference surface 416 and second reference surface 418 may be angled towards each other as they extend from the top surface 404 to the bottom surface 406. The angle of the reference surfaces 416, 418 determines the size of the bone segment that will be cut out from the metatarsal bone 12. As depicted in the embodiment of FIG. 21, the second reference surface 418 has a larger angle than the first reference surface 416, although in other embodiments the first reference surface 416 may have a larger angle than the second reference surface 418 and both the first and second reference surfaces 416, 418 may have the same angles. The guide 400 may also include a cutout 420 at the second end 410 to allow for visualization of a portion of the bone 12 during surgery.

Another guide embodiment 500 is shown in FIGS. 22A-22F and 27-30. The guide 500 may include a plate 502 with a first end 504 and a second end 506. The first end 504 may be a distal end of the plate 502 and the second end 506 may be a proximal end of the plate 502. The plate 502 may further include a medial portion extending between the first end 504 and the second end 506. The guide 500 may be, for example, tapered from the first end 504 to the second end 506 along its length. The first end 504 of the guide 500 may have a width, for example, greater than the width of the second end 506.

The guide 500 may also include at least one opening 508. In the depicted embodiment there are two openings 508, near the first end 504. The at least one opening 508 may be, for example, surrounded by screw sleeves or bushings 509 extending out from the plate 502 near the first end 504. The screw sleeves 509 may be integral with the plate 502 or removable from the plate 502 to allow for modular construction. The screw sleeves 509 may be configured to facilitate alignment of drilling openings in a patient's bones. The openings drilled in a patient's bone using screw sleeves 509 may receive, for example, temporary fixation members during use of the guide 500 and/or a portion of an implant, such as implant 100, 900, 920, 940, 980, once the guide 500 is removed. The screw sleeves 509 may also be used as a depth guide when drilling the openings for the engagement portions 104, 904, 924, 944, 984 of the implants 100, 900, 920, 940, 980.

The guide 500 may also include at least one hole 510 through the plate 502 near the at least one opening 508 that is proximate the first end 504. The hole 510 may be relatively centered between the openings 508. The guide 500 may further include a first notch 512 in the side of plate 502 and a second notch 514 in an opposite side of plate 502. Although the first notch 512 and second notch 514 are shown as semi-circles, other shapes for the notches 512, 514 are also contemplated. In addition, the guide 500 may include at least one aperture 516 in the plate 502. In the embodiment shown there is one aperture 516 which may be, for example, along the longitudinal axis of the plate 502 between the notches 512, 514 and the second end 506.

As shown in FIGS. 22A-22F, the guide 500 may also include a first tab 518 at the first end 504 of the plate 502 and a second tab 520 at the second end 506 of the plate 502. The first tab 518 may have, for example, a generally triangular shape. The first tab 518 may also be, for example, curved as it extends out from the first end 504 of the plate 502 from a top surface of the plate 502 down past the bottom surface of the plate 502. The second tab 520 may have, for example, a generally triangular shape. The second tab 520 may also be, for example, curved as it extends out from the second end 506 of the plate 502 from a top surface of the plate 502 down past the bottom surface of the plate 502. The first tab 518 may be positioned in a first cutout 522 between the openings 508 and the second tab 520 may be positioned in a second cutout 524. The cutouts 522, 524 may assist the surgeon with visualization of a metatarsal bone and the tabs 518, 520 may assist the surgeon with alignment of the guide 500 relative to the metatarsal bone and initial fixation of the guide to the bone to be cut. The first and second cutouts 522, 524 may have, for example, a generally rectangular shape, although other shapes that provide sufficient visualization are also contemplated. The guide 500 may further include at least one alignment line 525 to assist with alignment of the guide 500 and to provide a visual indication of where the cuts to the bone will be made.

Figure 23A:
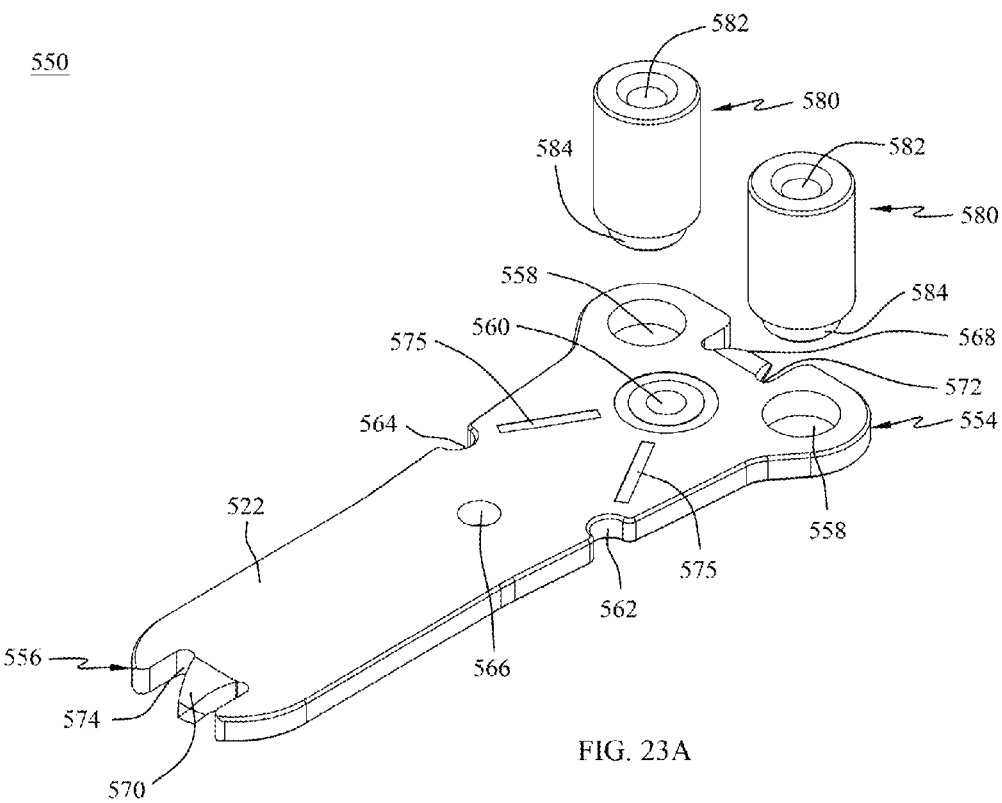
FIG. 23A is an exploded top perspective view of another guide, in accordance with an aspect of the present invention.
Figure 23B:
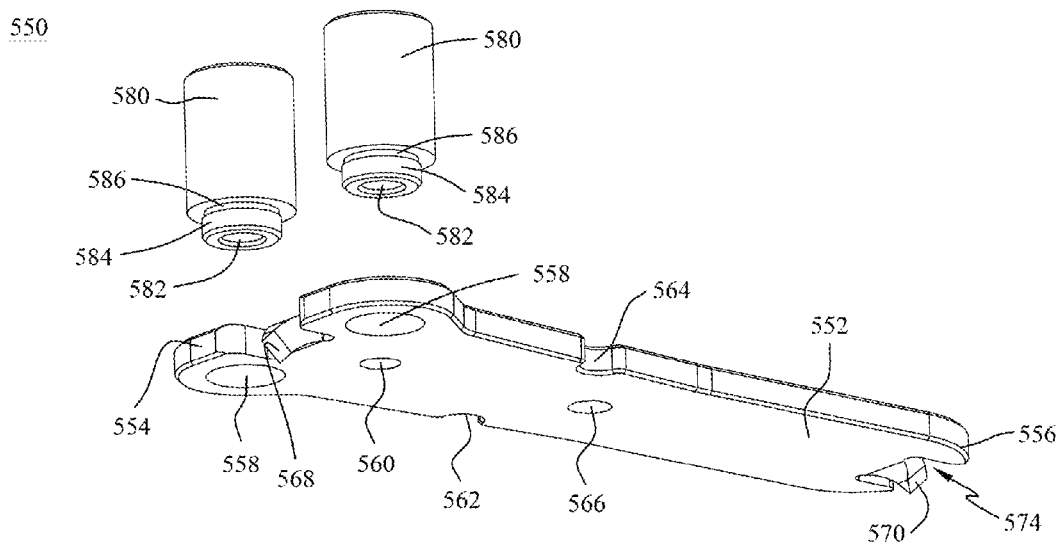
FIG. 23B is an exploded bottom perspective view of the guide of FIG. 23A, in accordance with an aspect of the present invention.

Referring now to FIGS. 23A and 23B, another guide 550 is shown. The guide 550 may include a plate 552 with a first end 554 and a second end 556. The first end 554 may be, for example, a distal end of the plate 552 and the second end 556 may be, for example, a proximal end of the plate 552. The medial portion may extend between the first end 554 and the second end 556 of the plate 550. The guide 550 may be, for example, tapered along its length from the first end 554 to the second end 556. The width at the first end 554 of the guide 550 may be, for example, greater than the width of the second end 556.

The guide 550 may also include at least one opening 558 in the first end 554 of the plate 552. In the depicted embodiment there are two openings 558. The at least one opening 558 may be sized and shaped to receive at least one screw sleeves 580. The screw sleeves 580 may have, for example, a hole 582 extending from a top surface to a bottom surface and an extension or boss 584 to couple the screw sleeve 580 to the plate 552. The extension 584 of the screw sleeves 580 may be inserted into the openings 558 in the plate 552. As shown in FIGS. 24A-24C, the screw sleeves 580 may also include a circumferential groove 586 positioned where the flange 584 secures to the body of the screw sleeve 580. The hole 582 may include a tapered edge 588 at the first end of the screw sleeve 580. The screw sleeves 580 may be configured to facilitate alignment of drilling openings in a patient's bones. The openings drilled in a patient's bone using screw sleeves 580 may receive, for example, temporary fixation members during use of the guide 550 and/or a portion of an implant, such as implant 100, 900, 920, 940, 980, once the guide 550 is removed. The screw sleeves 580 may also be used as a depth guide when drilling the openings for the engagement portions 104, 904, 924, 944, 984 of the implants 100, 900, 920, 940, 980.

The guide 550 may also include at least one hole 560 through the plate 552 near the at least one opening 558 that is proximate the first end 554. The hole 560 may be relatively centered between the openings 558. The guide 550 may further include a first notch 562 in the side of plate 552 and a second notch 564 in an opposite side of plate 502. The first notch 562 and second notch 564 may be of the type described above with reference to first notch 512 and second notch 514, which will not be described again here for brevity sake. The guide 550 may include at least one aperture 566 in the plate 552. In the embodiment shown there is one aperture 566 which may be, for example, along the longitudinal axis of the plate 552 between the notches 562, 564 and the second end 556.

With continued reference to FIGS. 23A-23B, the guide 550 may also include a first tab 568 at the first end 554 of the plate 552 and a second tab 570 at the second end 556 of the plate 552. The first tab 568 and the second tab 570 may be of the type described above with reference to first tab 518 and second tab 520, which will not be described again here for brevity sake. The guide 550 may also include a first cutout 572 at the first end 554 and a second cutout 574 at the second end 556. The first cutout 572 and second cutout 574 may be of the type described above with reference to the first cutout 522 and second cutout 524, respectively, which will not be described again here for brevity sake. The guide 550 may further include at least one alignment line 575 to assist with alignment of the guide 550 and to provide a visual indication of where the cuts to the bone will be made.

Another embodiment of a screw sleeve 590 is shown in FIGS. 25A-25C. The screw sleeve 590 may be used in place of screw sleeve 580. The screw sleeve 590 may include an extension or boss 594 extending out from a bottom end of the sleeve 590 with, for example, a smaller diameter than the rest of the screw sleeve 590. The screw sleeve 590 may also include a hole 592 extending from the top end to the bottom end. The hole 592 may include a tapered edge 596 at the top end of the screw sleeve 590. The extension 594 of the sleeve 590 may couple to the at least one opening 558 in the plate 502 shown in FIGS. 23A-23B. The screw sleeves 590 may be configured to facilitate alignment of drilling openings in a patient's bones. The openings drilled in a patient's bone using screw sleeves 590 may receive, for example, temporary fixation members during use of the guide 550 and/or a portion of an implant, such as implant 100, 900, 920, 940, 980, once the guide 550 is removed. The screw sleeves 590 may also be used as a depth guide when drilling the openings for the engagement portions 104, 904, 924, 944, 984 of the implants 100, 900, 920, 940, 980.

Figure 26:
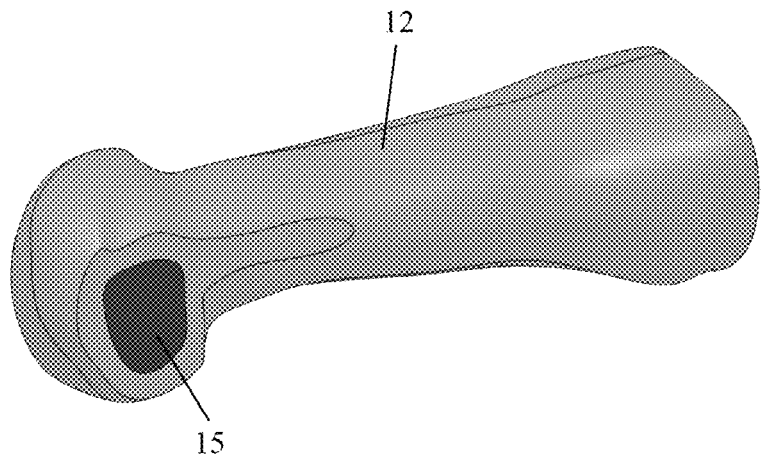
FIG. 26 is a medial perspective view of a first metatarsal bone with a hallux valgus deformity removed, in accordance with an aspect of the present invention.
Figure 27:
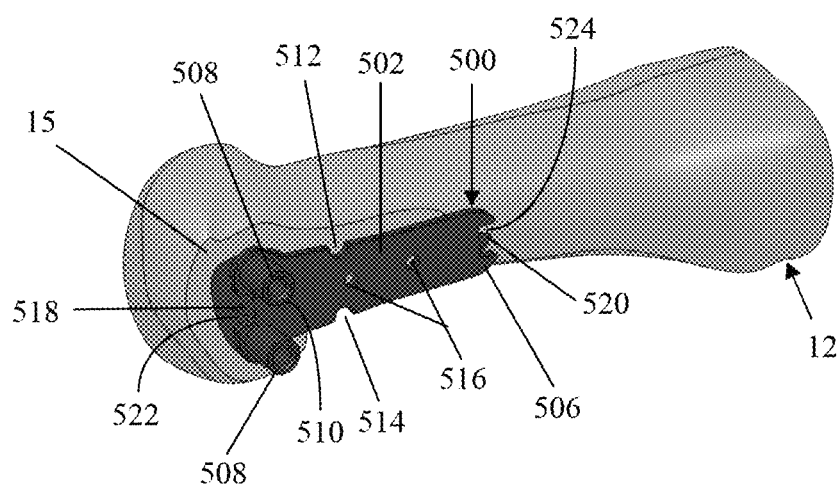
FIG. 27 is a medial perspective view of the first metatarsal bone of FIG. 26 with a bone cutting guide, in accordance with an aspect of the present invention.

Referring now to FIGS. 26-31, a method of using the guide 500 to cut a patient's metatarsal bone 12 is shown. The guide 550 may also be used in place of guide 500 as described below, which will not be described here for brevity sake. FIG. 26 shows the metatarsal bone 12 after an exostectomy surgical procedure was performed leaving a relatively flat bone surface 15 where the bunion was removed from the metatarsal bone 12. An osteotomy may then be performed to realign the patient's bones 12, 13 (see FIG. 1) using the guide 500 as shown in FIGS. 27-31. The guide 500 may be aligned over the bone surface 15 of the metatarsal bone 12, as shown in FIG. 27. The tabs 518, 520 may be used to assist the surgeon with aligning the guide 500 on the metatarsal bone 12.

Figure 28:
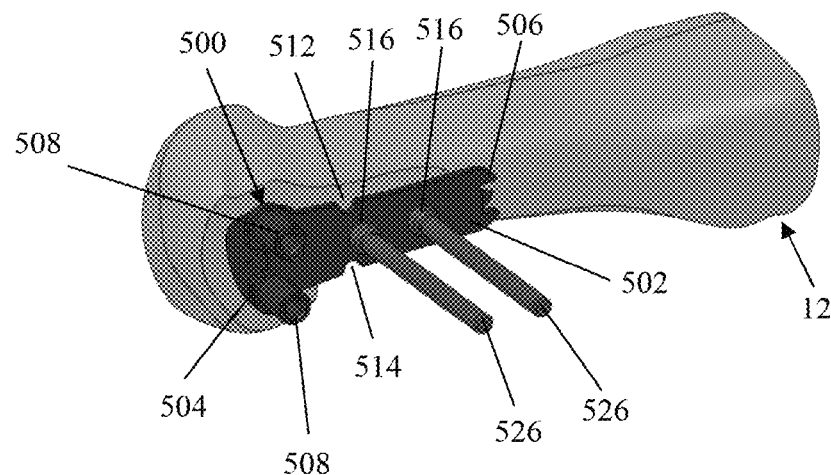
FIG. 28 is a medial perspective view of the first metatarsal bone and guide of FIG. 27 with temporary fixation mechanisms holding the guide to the bone, in accordance with an aspect of the present invention.

Once the guide 500 is aligned in the desired position on the metatarsal bone 12, at least one temporary fixation device 526 may be inserted through an aperture 516 and into the metatarsal bone 12. As shown in FIG. 28, two temporary fixation devices 526 are inserted through the two apertures 516 to hold the guide 500 to the metatarsal bone 12 during at least a portion of the osteotomy procedure. After securing the guide 500 to the metatarsal bone 12, imaging techniques, for example fluoroscopy, may be performed to confirm the placement or alignment of the guide along the metatarsal bone 12.

Figure 29:
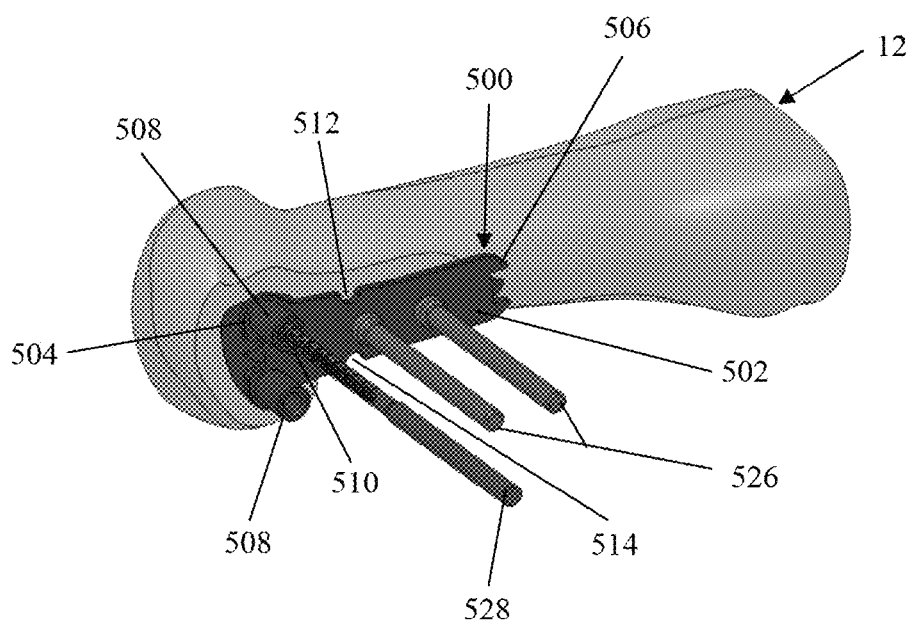
FIG. 29 is a medial perspective view of the first metatarsal bone and guide of FIG. 27 with temporary fixation mechanisms holding the guide to the bone and an inserted drill bit, in accordance with an aspect of the present invention.
Figure 30:
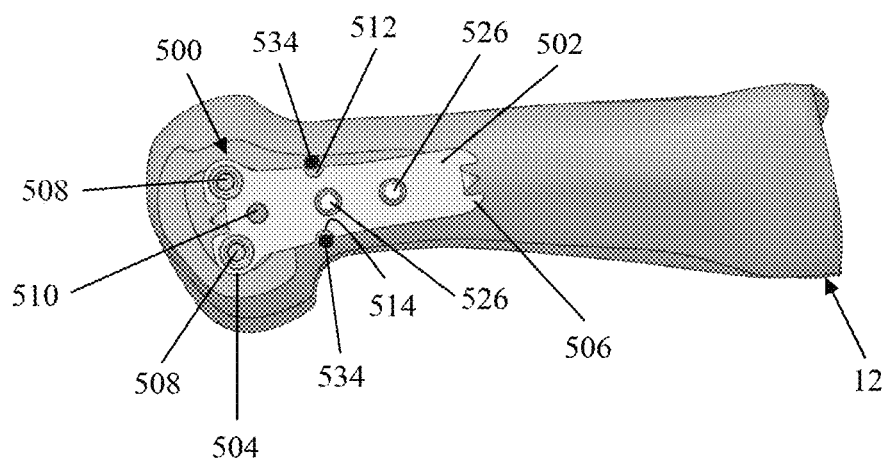
FIG. 30 is a medial perspective view of the first metatarsal bone and guide of FIG. 27 showing two bone cut markings, in accordance with an aspect of the present invention.

Referring now to FIG. 29, once the desired placement or alignment of the guide 500 is achieved, a drill 528 may be inserted through openings 508 and hole 510 to drill holes into the metatarsal bone 12. The drill 528 may be inserted through openings 508 to drill holes 530 (see FIG. 31) into the metatarsal bone 12. The holes 530 may be drilled to a desired depth, which may be, for example, until contact with the lateral cortex. The drill 528 may also be inserted through hole 510 to drill hole 532 (see FIG. 31) to a desired depth in the metatarsal bone 12. The desired depth for hole 532 may be, for example, all the way through the metatarsal bone 12. Next, the surgeon may optionally place marks 534 onto the metatarsal bone 12 where the notches 512, 514 are located, as shown in FIG. 30. After the holes 530 and 532 are drilled and the marks 534 are placed onto the bone, the guide 500 may be removed from the metatarsal bone 12 by removing the temporary fixation devices 526.

Figure 31:
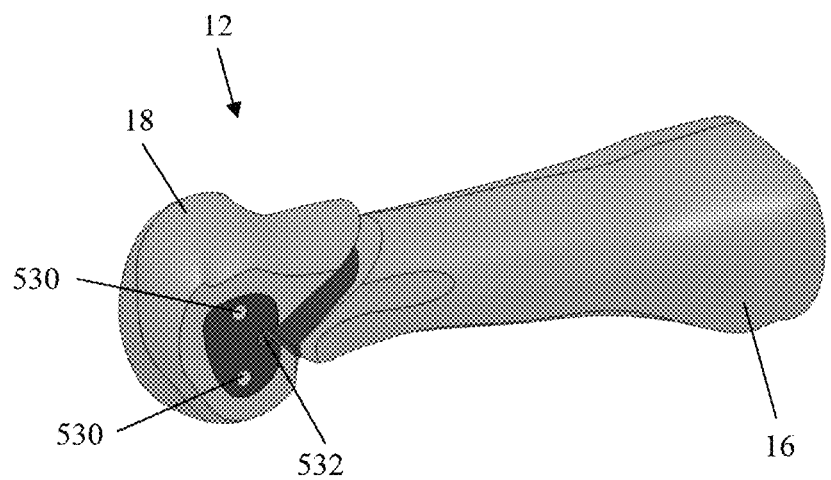
FIG. 31 is a medial perspective view of the first metatarsal bone of FIG. 26 showing the bone cuts, in accordance with an aspect of the present invention.

The hole 532 drilled through hole 510 into the metatarsal bone 12 may be used by a surgeon as a guide for cutting the metatarsal bone 12. If the optional marks 534 were made on the metatarsal bone 12 using notches 512, 514, the marks 534 may be used with the hole 532 as a guide for the surgeon while cutting the metatarsal bone 12. FIG. 31 shows the metatarsal bone 12 after the cuts are made creating a first bone segment 16 and a second bone segment 18. As illustrated in FIG. 31, the first bone segment 16 is the proximal end of the metatarsal bone 12 and the second bone segment 18 is the distal end of the metatarsal bone 12. The first and second bone segments 16, 18 may then be aligned, for example, by moving the first bone segment 16 laterally with respect to the second bone segment 18, and then compressed.

Figure 33:
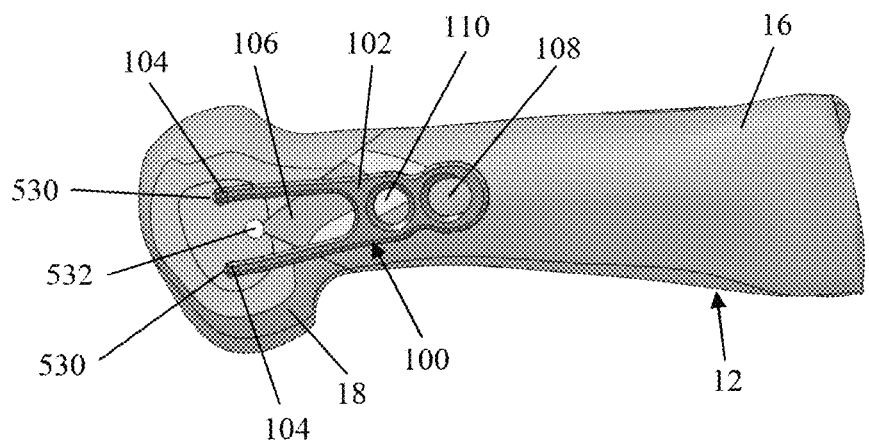
FIG. 33 is a medial view of the first metatarsal bone of FIG. 26 with the implant of FIG. 32, in accordance with an aspect of the present invention.

After the desired alignment and compression of the metatarsal bone 12 is achieved, an implant 100 may be inserted and secured to the metatarsal bone 12, as shown in FIGS. 33-36. The implant 100, shown in FIG. 32, is described in greater detail above and for brevity sake will not be described again here. As shown in FIG. 33, the engagement portions 104 of the implant 100 may be inserted into the holes 530 in the second segment 18 of metatarsal bone 12. Once the engagement portions 104 are inserted into the holes 530, the opening 106 may be aligned over the cuts in the metatarsal bone 12 enabling visualization of the alignment of the first and second bone segments 16, 18. In addition, the compression slot 108 and aperture 110 may be aligned over the first bone segment 16.

Figure 34:
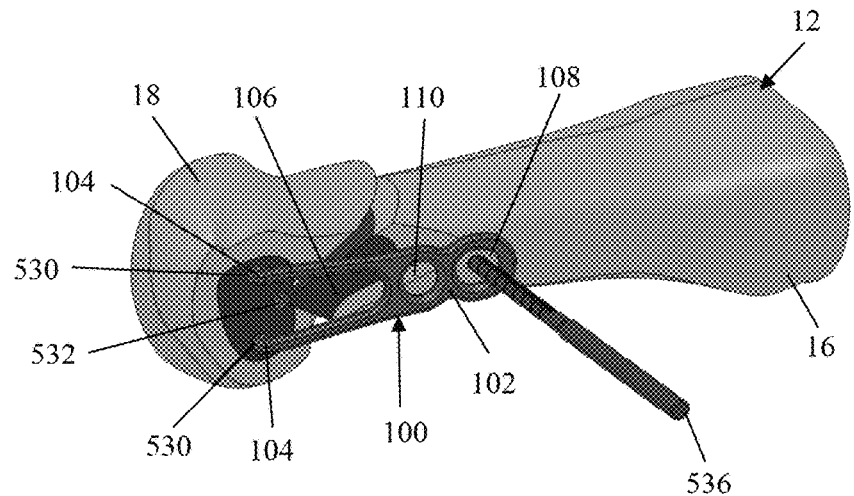
FIG. 34 is a medial perspective view of the first metatarsal bone and implant of FIG. 33 including a drill bit, in accordance with an aspect of the present invention.
Figure 35:
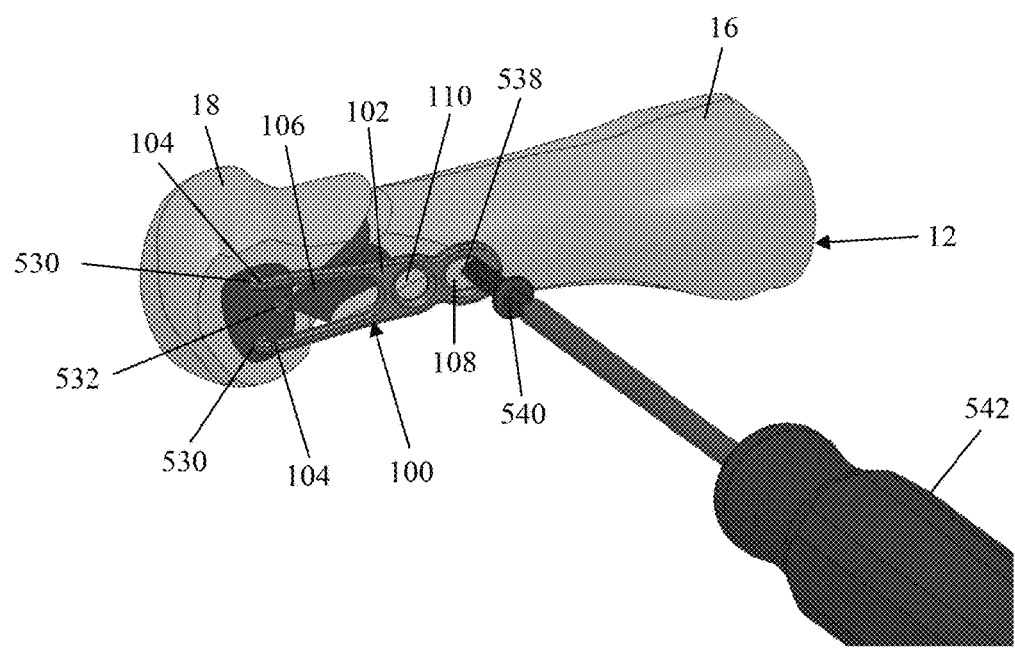
FIG. 35 is a medial perspective view of the first metatarsal bone and implant of FIG. 33 including a fastener and insertion device, in accordance with an aspect of the present invention.
Figure 36:
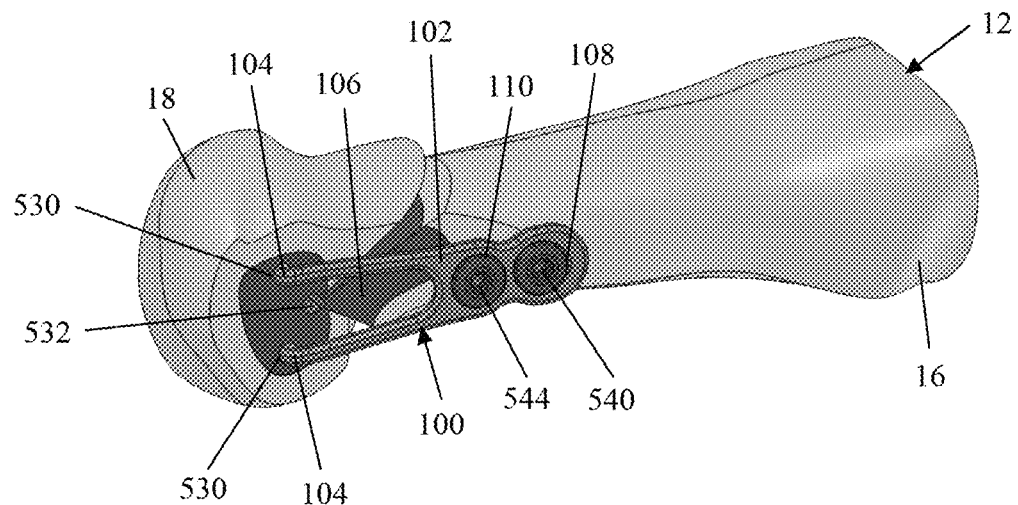
FIG. 36 is a medial perspective view of the implant of FIG. 33 inserted on the first metatarsal bone and secured with two fasteners, in accordance with an aspect of the present invention.

Referring now to FIGS. 34-36, the implant 100 may then be fixed to the metatarsal bone 12. As shown in FIG. 34, a drill 536 may be inserted through the compression slot 108 and into the metatarsal bone 12 to drill a pilot hole 538 for a bone fastener 540 (see FIG. 35). The drill 536 may be inserted, for example, into the proximal end of the compression slot 108 and into the first bone segment 16 of the metatarsal bone 12 which has been manually compressed. The pilot hole 538 may then be drilled into the first bone segment 16, for example, across the lateral cortex.

Once the pilot hole 538 is drilled, a bone fastener 540 may be inserted into the pilot hole 538 through compression slot 108 which is configured to cause a compressive load to be applied across the osteotomy using, for example, a screw driver 542, as shown in FIG. 35. The bone fastener 540 may be, for example, a bone screw. As the bone fastener 540 is screwed into the bone 12, the bone fastener 540 will slide along the compression slot 108 providing additional compression of the first and second bone segments 16, 18. The compression slot 108 may provide, for example, an additional about 1 mm to about 5 mm of reduction.

After the bone fastener 540 is screwed into the bone 12 through compression slot 108 to apply the compressive force, a second bone fastener 544 may optionally be inserted through aperture 110 and into the first bone segment 16, as shown in FIG. 36. The second bone fastener 544 may also be inserted into the metatarsal bone 12 using a drill 536 to drill a pilot hole, not shown, for insertion of the second fastener 544 through aperture 110 using a screw driver 542.

Figure 37:
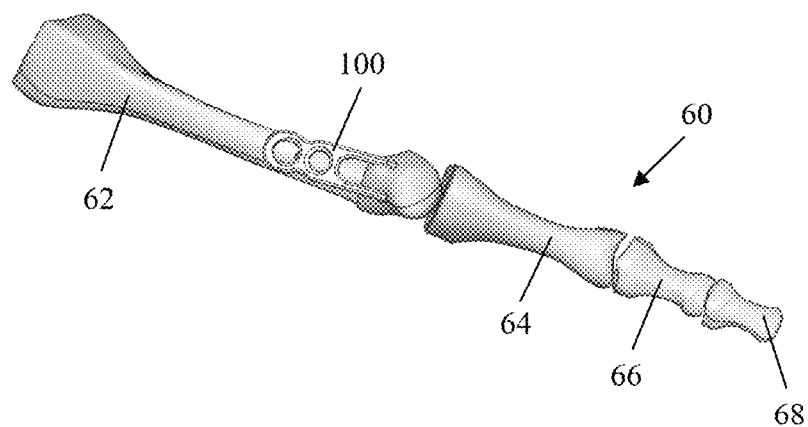
FIG. 37 is a view of the implant of FIG. 32 attached to a second, third, or fourth metatarsal bone, in accordance with an aspect of the present invention.
Figure 38:
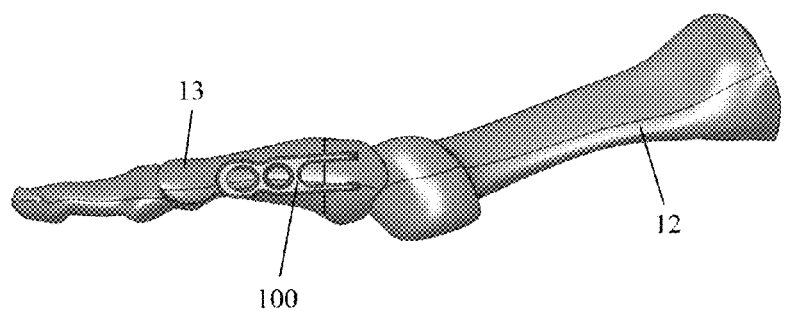
FIG. 38 is a medial view of the implant of FIG. 32 attached to a proximal phalanx bone of a hallux, in accordance with an aspect of the present invention.

Referring now to FIG. 37, the common bones of a second, third, fourth, or fifth toe are shown. The toe 60 may include a metatarsal bone 62, a proximal phalanx 64, a middle phalanx 66, and a distal phalanx 68. An implant 100 is shown inserted into the metatarsal bone 62 at a distal end. The implant 100 will be attached to the metatarsal bone 62 as described above with reference to guide 500, and for brevity sake will not be described again here. FIG. 38 shows another embodiment of correcting the alignment of a toe with the implant 100. The implant 100 may be secured to the proximal end of the proximal phalanx 13 of the great toe, as shown in FIG. 38. The implant 100 is of the type described above and for brevity sake will not be described again here.

Figure 39:
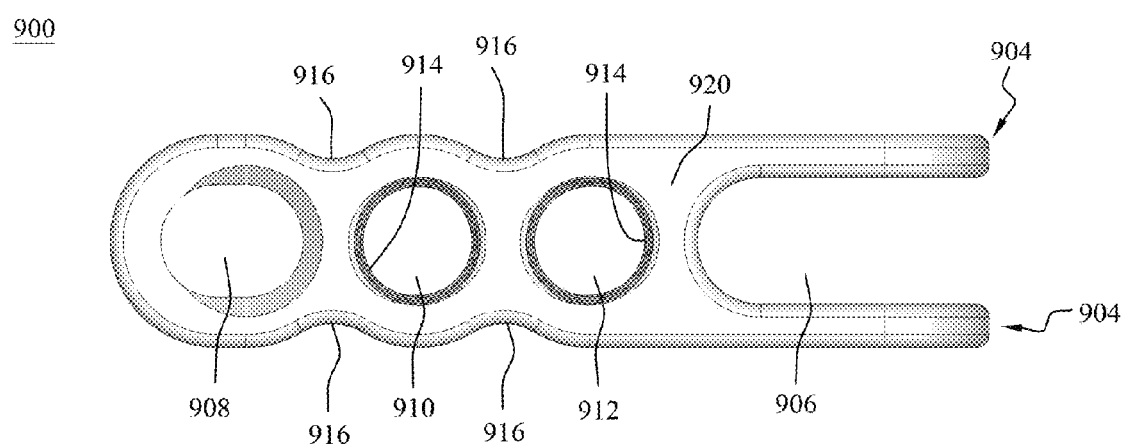
FIG. 39 is a top view of another embodiment of an implant, in accordance with an aspect of the present invention.
Figure 41A:
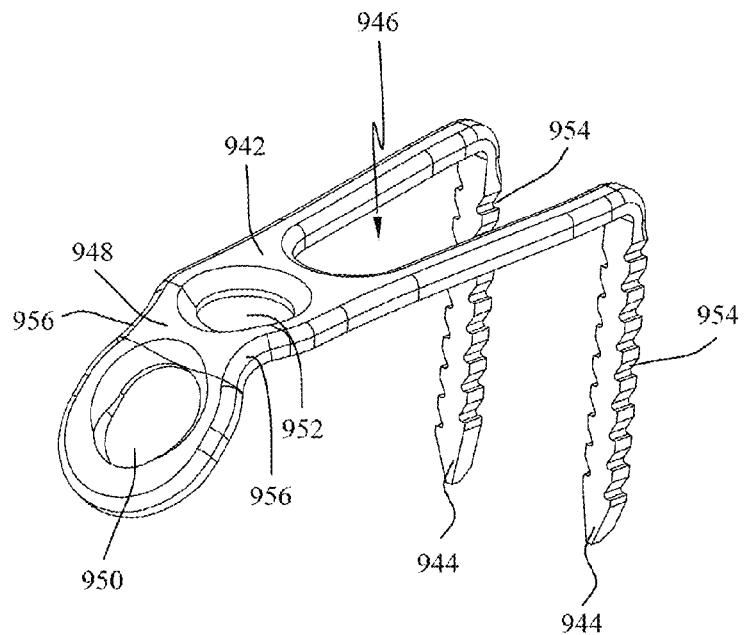
FIG. 41A is a top perspective view of another implant, in accordance with an aspect of the present invention.
Figure 41B:
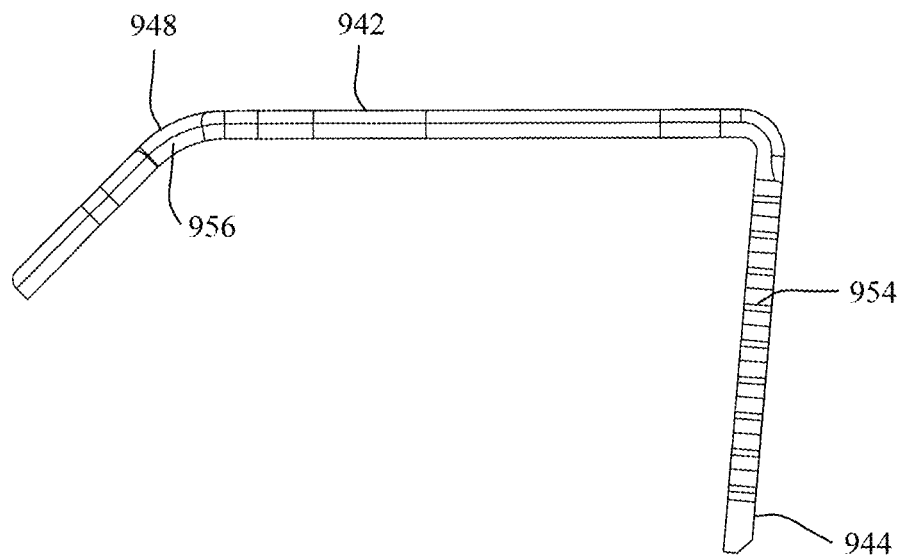
FIG. 41B is a side view of the implant of FIG. 41A, in accordance with an aspect of the present invention.
Figure 41C:
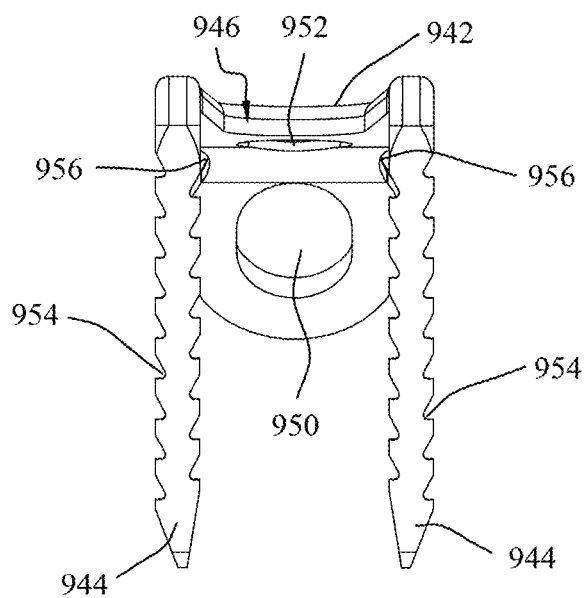
FIG. 41C is a first end view of the implant of FIG. 41A, in accordance with an aspect of the present invention.
Figure 41D:
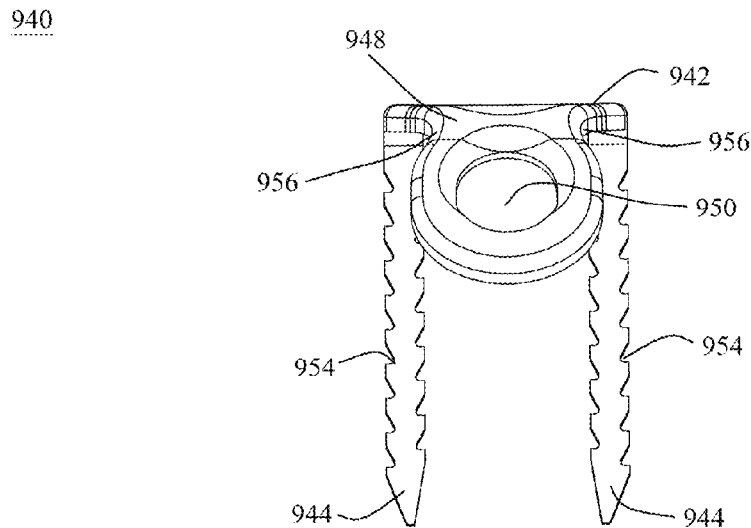
FIG. 41D is a second end view of the implant of FIG. 41A, in accordance with an aspect of the present invention.
Figure 42:
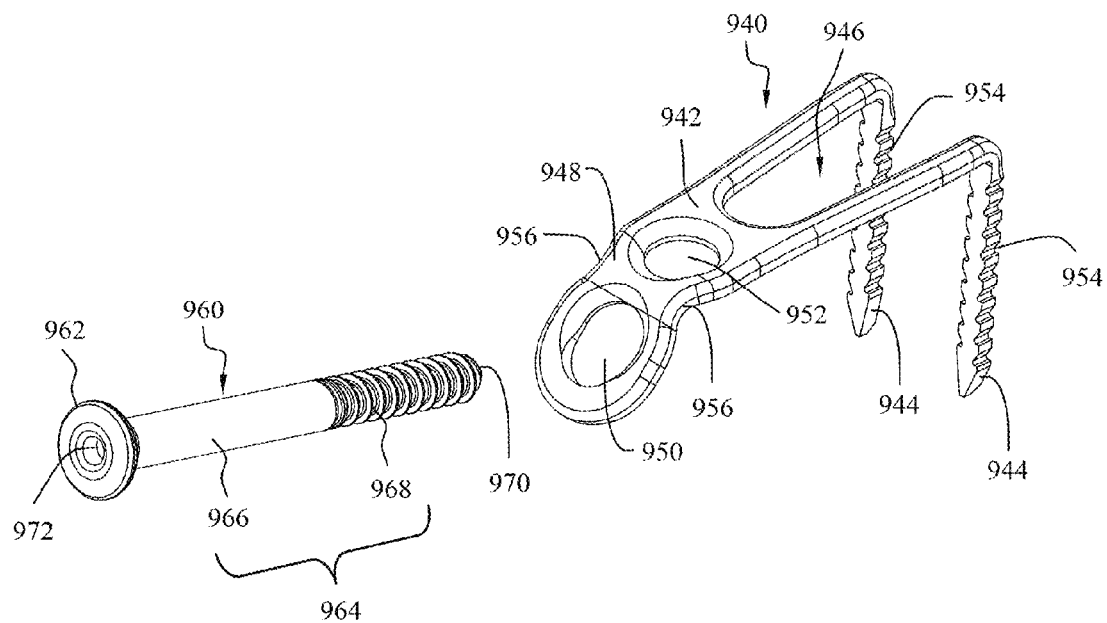
FIG. 42 is an exploded, top perspective view of an implant system including the implant of FIG. 41A and a fastener, in accordance with an aspect of the present invention.
Figure 43:
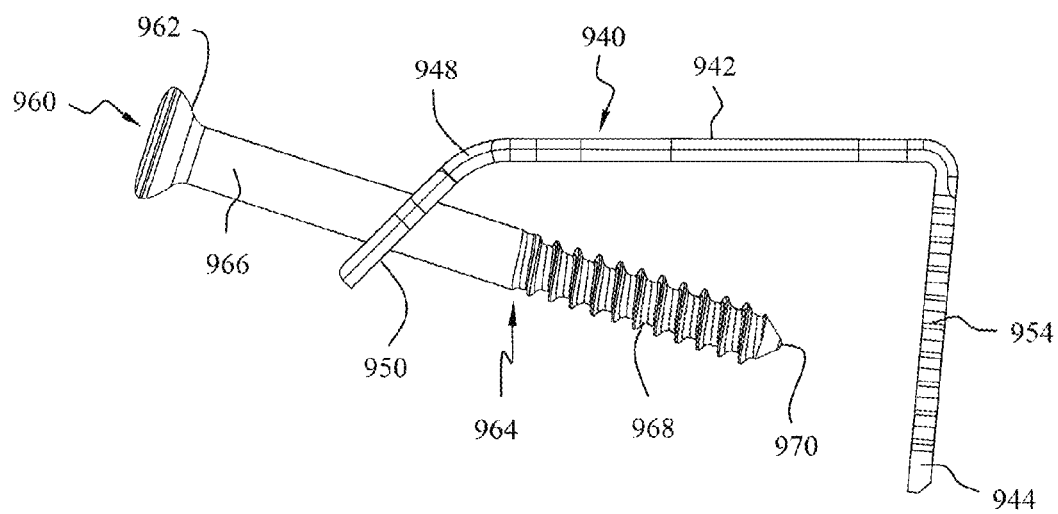
FIG. 43 is a partially exploded, side view of the implant system of FIG. 42, in accordance with an aspect of the present invention.
Figure 44:
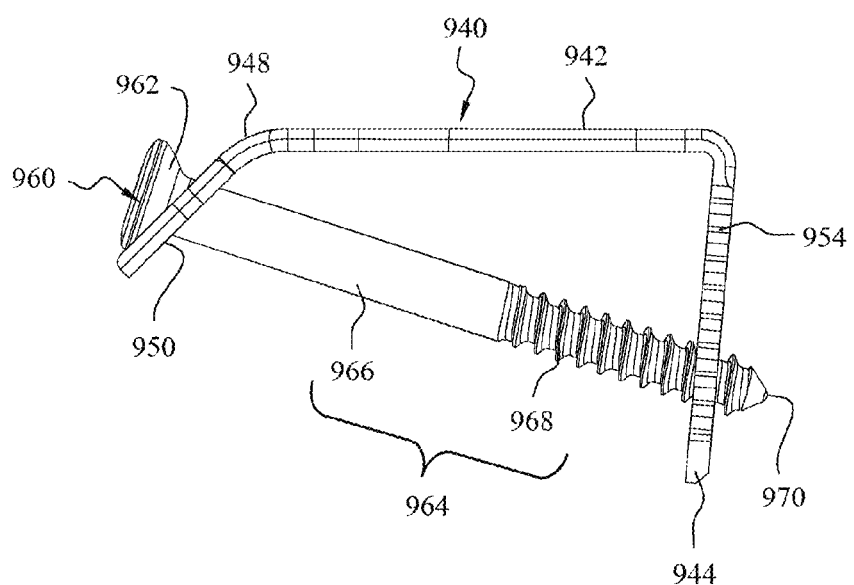
FIG. 44 is a side assembled view of the implant system of FIG. 42, in accordance with an aspect of the present invention.
Figure 45:
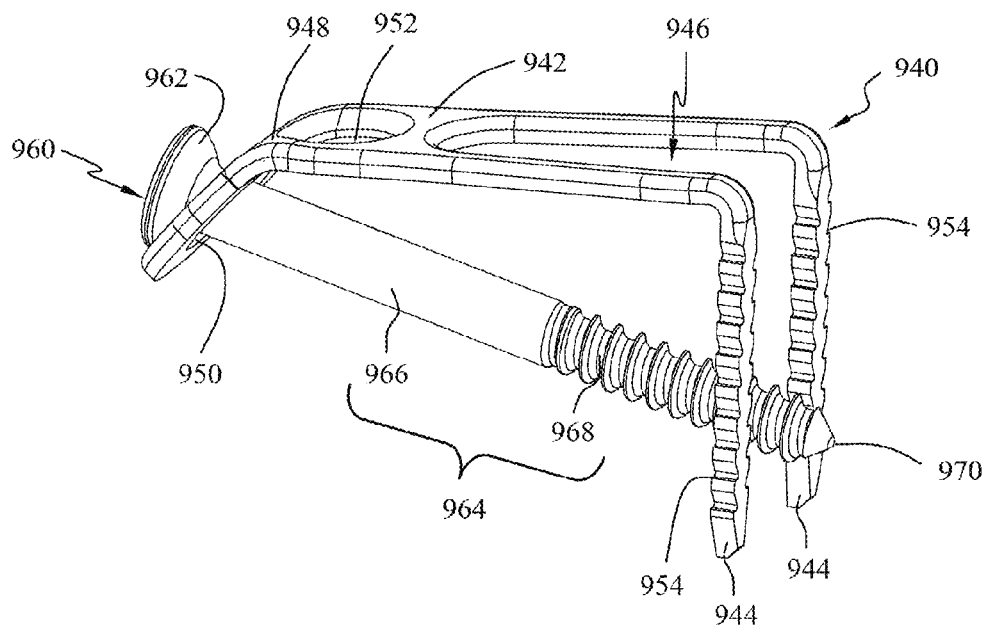
FIG. 45 is a side perspective assembled view of the implant system of FIG. 42, in accordance with an aspect of the present invention.
Figure 46:
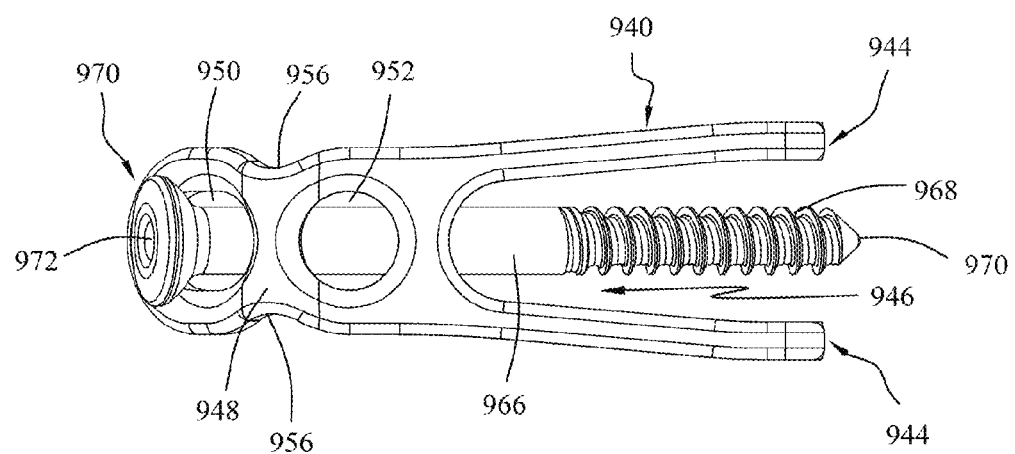
FIG. 46 is a top perspective assembled view of the implant system of FIG. 42, in accordance with an aspect of the present invention.

FIG. 39 shows another implant 900 including a body member 902 with at least one engagement portion 904 extending relatively perpendicular from the body member 902. As shown in one embodiment, the implant 900, for example, includes two engagement portions 904. The two engagement portions 904 extend, for example, relatively normal from the body member 902. The two engagement portions 904 may also be positioned, for example, parallel to each other. The body member 902 may also include at least one space 906 in the distal portion of the implant 900 defined by opposing engagement portions 904. The space 906 may enable visualization of the at least two bone segments when the implant 900 is inserted into a patient. In addition, the body member 902 may include at least one slot 908, for example a compression slot, allowing for movement of a first bone segment relative to a second bone segment as a first bone fastener (not shown) is inserted into the compression slot 908. The compression slot 908 is configured to facilitate the application of a compressive force across an osteotomy when the bone fastener is tightened. The body member 902 may also include at least one aperture, for example, a first aperture 910 and a second aperture 912. Although only two apertures 910, 912 are shown, a plurality of apertures 910, 912 in the implant 900 are contemplated. The first and second apertures 910, 912 may receive at least one second fastener (not shown). The at least one second fastener may be inserted after the first fastener has completed the desired compression of the first and second bone segments. The apertures 910, 912 may include, for example, threads 914, such as, locking threads. The threads 914 may be sized to engage corresponding threads on a fastener to secure the fastener in the apertures 910, 912 of the body member 902. The at least one engagement portion 904 may include engagement members (not shown) to assist in holding the engagement portions 904 in the holes in a bone segment. The engagement members may be, for example, ridges, barbs, spikes, and teeth-like or tine-like structures located along the length of the engagement portions 904 (similar to ones shown in FIG. 41A). The body member 902 may have, for example, a generally rectangular or oval shape with indents or grooves 916 on each side of the body member 902 and positioned between each of the compression slot 908 and the apertures 910, 912. The implants 900 may come in a variety of sizes to correspond to the different size metatarsal bones in people.

Figure 40:
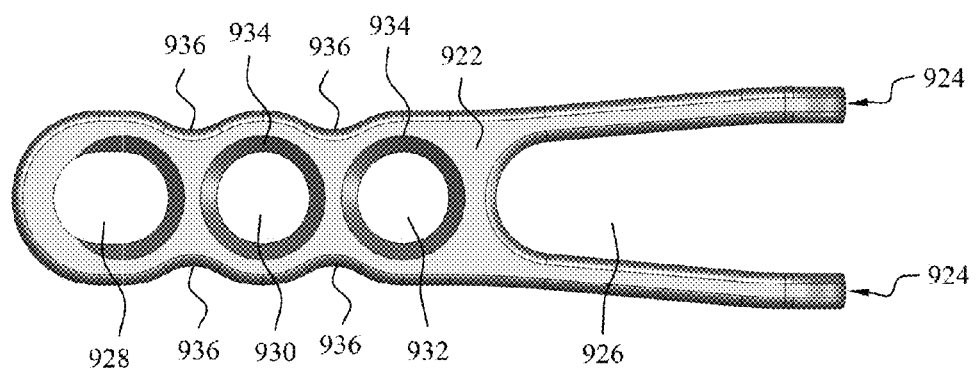
FIG. 40 is a top view of yet another embodiment of an implant, in accordance with an aspect of the present invention.

Referring now to FIG. 40, another implant 920 is shown. The implant 920 may be of the type described above with reference to implant 900. The implant 920 may include a body member 922 with at least one engagement portion 924 defining or creating at least one space 926 at a first end and a compression slot 928 at a second end. The body member 922, at least one engagement portion 924, at least one space 926, and compression slot 928 may be of the type described above with reference to body member 902, engagement portion 904, at least one space 906, and compression slot 928, respectively, which will not be described again here for brevity sake. However, unlike engagement portions 904, the engagement portions 924 may diverge from each other as they extend away from the body member 922. Although not shown, it is also contemplated that the engagement portions 924 may converge on each other. The engagement portions 924 may also be positioned in a relatively perpendicular orientation from the body member 922. The engagement portions 924 may extend, for example, relatively normal from the body member 922. The engagement portions 924 may also be positioned, for example, parallel to each other. The at least one engagement portion 924 may include engagement members (not shown) to assist in holding the engagement portions 924 in the holes in a bone segment. The engagement members may be, for example, ridges, barbs, spikes, and teeth-like or tine-like structures located along the length of the engagement portions 924 (similar to ones shown in FIG. 41A).

The implant 920 may also include at least one aperture, for example, a first aperture 930 and a second aperture 932. Although only two apertures 930, 932 are shown, a plurality of apertures 930, 932 in the implant 920 are contemplated. The at least one aperture 930, 932 may be, for example, either in line or offset from each other. The first and second apertures 930, 932 may receive at least one second fastener (not shown). The at least one second fastener may be inserted after the first fastener in the compression slot 928 has completed the desired compression of the first and second bone segments. The apertures 930, 932 may include, for example, a tapered portion 934 surrounding the edge of the apertures 930, 932 on the top of the body member 922. The body member 922 may have, for example, a generally rectangular or oval shape with indents or grooves 936 on each side of the body member 922 and positioned between each of the compression slot 928 and the apertures 930, 932. The implants 920 may come in a variety of sizes to correspond to the different size metatarsal bones in people.

FIGS. 41A-41D show another implant 940 including a body member 942 with at least one engagement portion 944 with engagement members 954. The engagement members 954 may extend perpendicular to the body member 942 and parallel to each other. The engagement portions 944 may, for example, extend divergent to each other as they extend away from the body member 942. The engagement members 954 may assist in holding the engagement portions 944 in the holes formed in a bone segment. The engagement members 954 may have, for example, ridges, barbs, spikes, and teeth-like or tine-like structures located along the perpendicular length of the engagement portions 944. The body member 942 may also include at least one space 946 in the distal portion of the implant 940 defined or created by opposing engagement portions 944. In addition, the body member 942 may include at least one slot 950, for example, a compression slot, allowing for movement of a first bone segment relative to a second bone segment as a first bone fastener (not shown) is inserted into the compression slot 950. The body member 942 may also include an aperture 952 for inserting a second fastener (not shown) after the first fastener has completed the desired compression of the first and second bone segments. The body member 942, engagement members 944, at least one space 946, compression slot 950, and aperture 952 are of the type described above with reference to body member 102, engagement members 104, at least one opening 106, compression slot 108, and aperture 110, which will not be described again here for brevity sake.

The implant 940 may also include an angled portion 948 at a first end of the body member 942. The angled portion 948 may include the compression slot 950. The angled portion 948 may extend, for example, at an angle of approximately 0 and 80 degrees with respect to the top surface of the body member 942. The body member 942 may have, for example, a generally rectangular or oval shape with indents or grooves 956 on each side of the body member 942 and positioned between each of the compression slot 950 and the aperture 952. The implants 940 may come in a variety of sizes to correspond to the different size metatarsal bones in people.

An implant system including the implant 940 and at least one fastener 960 are shown in FIGS. 42-46. The implant 940 is of the type described above with reference to FIGS. 41A-41D, which will not be described again here for brevity sake. The fastener 960 may be, for example, a bone screw. The fastener 960 may include, for example, a head 962 and a shaft 964. The shaft 964 may include, for example, a smooth portion 966 and a threaded portion 968. The fastener 960 may further include a tip 970 and an opening 972 extending from the head 962 to the tip 970.

The fastener 960 may be inserted into the compression slot 950 of the implant 940, as shown in FIGS. 43-46. The angled compression slot 950 allows for insertion of the fastener 960 at an angle. The fastener 960 may be inserted, for example, at an angle tilted approximately 0 to 80 degrees from a top surface of the body member 942. The fastener 960 may be inserted obliquely through the compression slot 950, the axis of which has been altered to create a non-perpendicular pathway. For example, the fastener 960 may be inserted medial to lateral or lateral to medial and superior to inferior or inferior to superior. As the fastener 960 is inserted at an angle it may be inserted across a bone fracture line or remain positioned in only one fragment or segment of the bone. Once the fastener 960 is inserted through the compression slot 950, a second fastener (not shown) may be inserted through the aperture 952. The second fastener may be sized and/or angled to avoid contacting the first fastener 960.

Figure 47A:
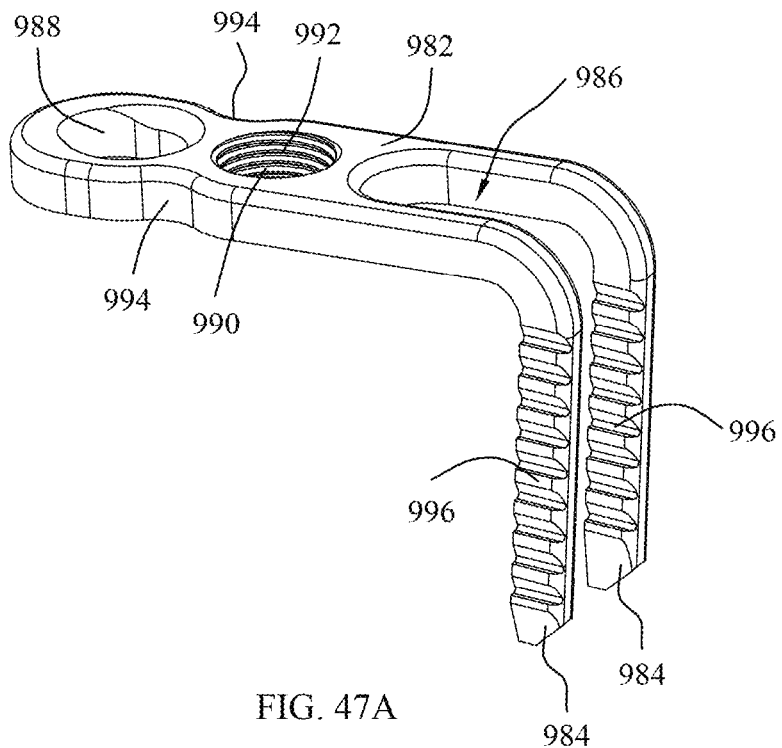
FIG. 47A is a perspective view of another implant, in accordance with an aspect of the present invention.
Figure 47B:
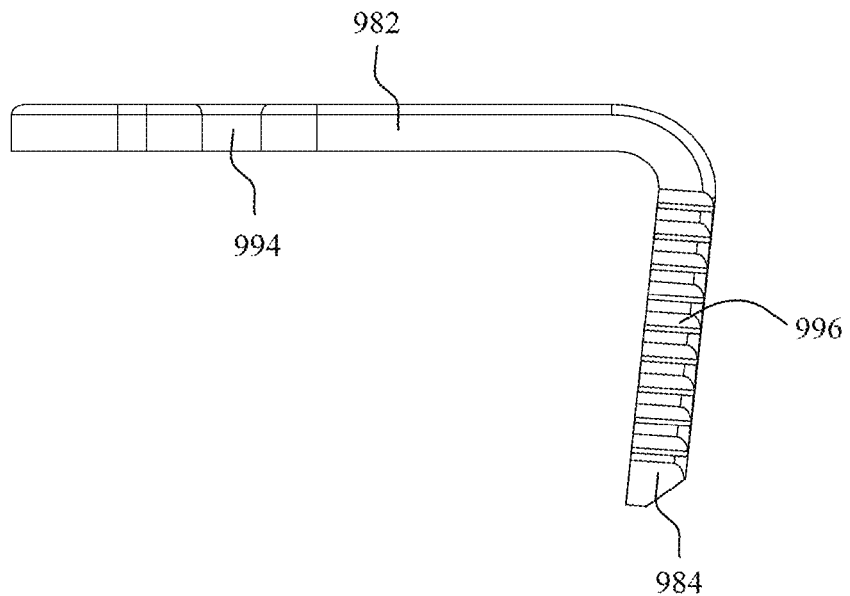
FIG. 47B is a side view of the implant of FIG. 47A, in accordance with an aspect of the present invention.
Figure 47C:
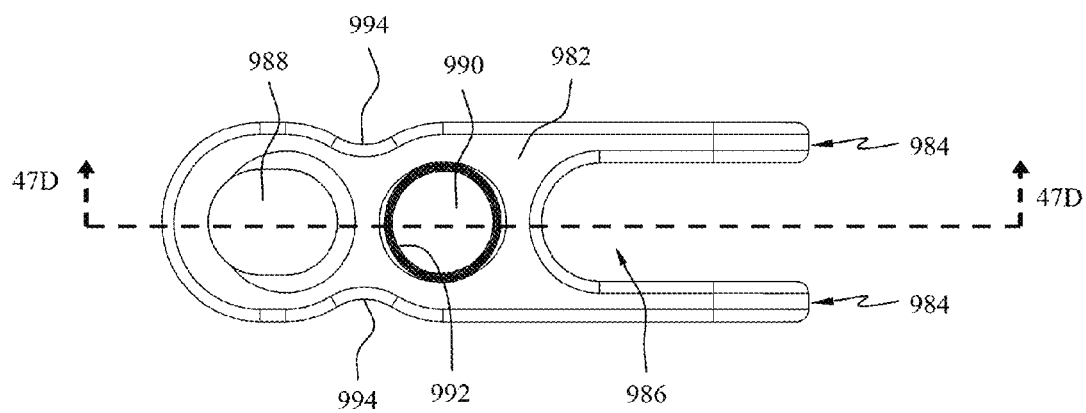
FIG. 47C is a top view of the implant of FIG. 47A, in accordance with an aspect of the present invention.
Figure 47D:
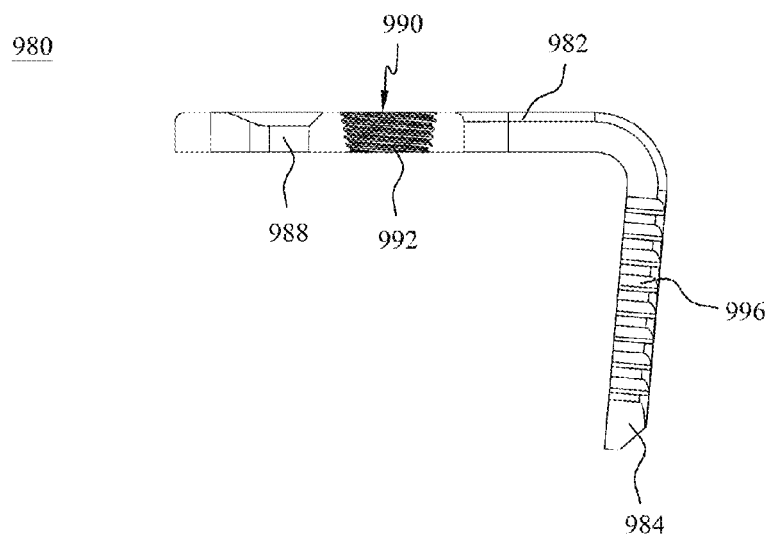
FIG. 47D is a side cross-sectional view of the implant of FIG. 47A taken along line 47D-47D in FIG. 47C, in accordance with an aspect of the present invention.
Figure 48A:
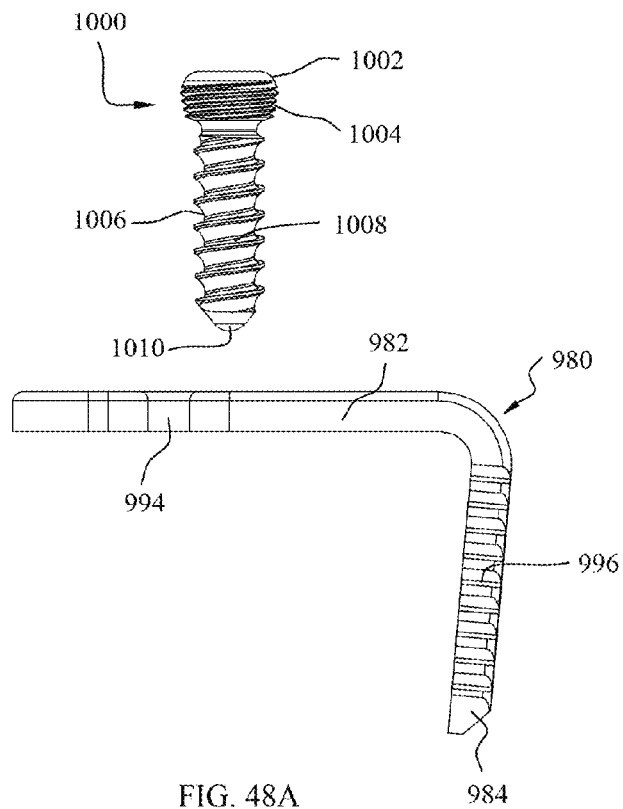
FIG. 48A is an exploded side view of an implant system including the implant of FIG. 47A and a fastener, in accordance with an aspect of the present invention.
Figure 48B:
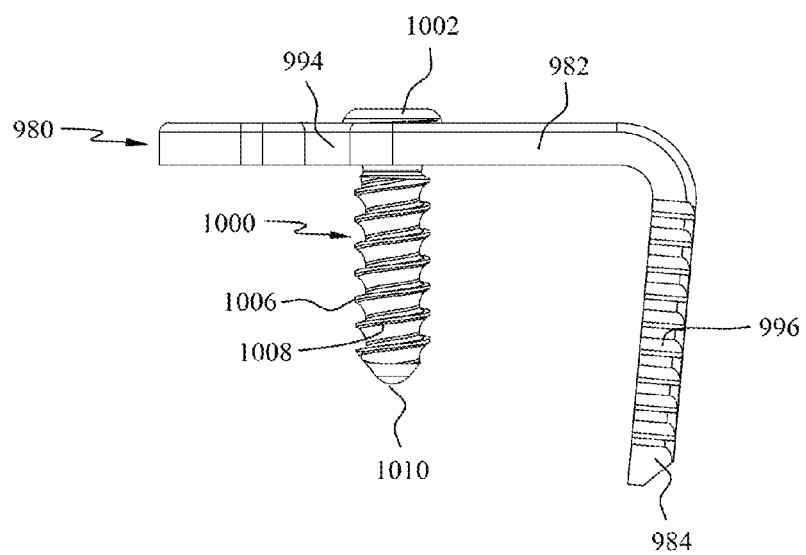
FIG. 48B is an assembled side view of the implant system of FIG. 48A, in accordance with an aspect of the present invention.
Figure 48C:
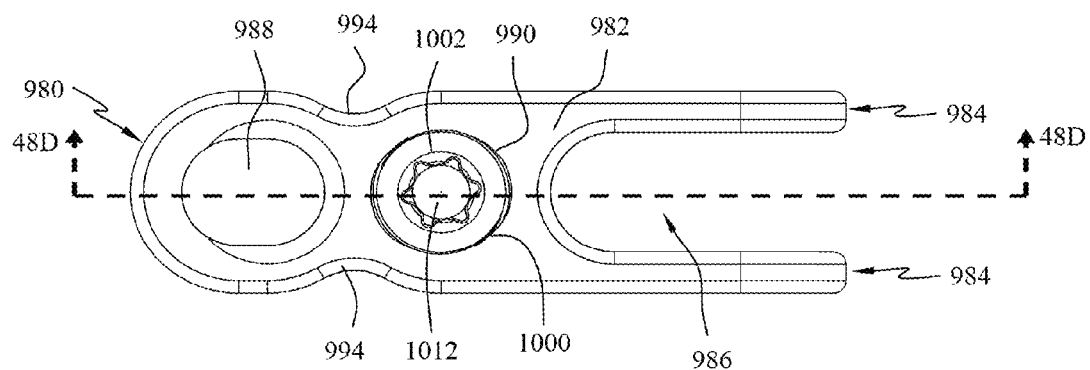
FIG. 48C is a top assembled view of the implant system of FIG. 48A, in accordance with an aspect of the present invention.
Figure 48D:
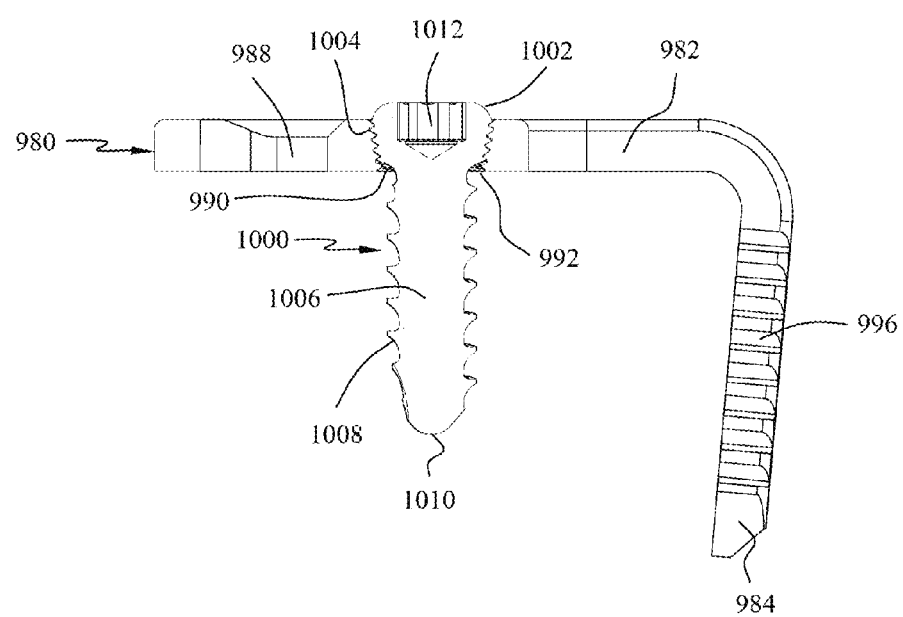
FIG. 48D is a side cross-sectional view of the assembled implant system of FIG. 48A take along line 48D-48D in FIG. 48C, in accordance with an aspect of the present invention.

Referring now to FIGS. 47A-47D, another implant 980 is shown. The implant 980 may be of the type described above with reference to implant 100. The implant 980 may include a body member 982 with at least one engagement portion 984 having engagement members 996. The body member 982 may also include at least one gap 986 defined or created by opposing engagement portions 984. In addition, the body member 982 may include at least one slot 988, for example, a compression slot, and an aperture 990. The body member 982, engagement portion 984, engagement members 996, at least one gap 986, compression slot 988, and aperture 990 are of the type described above with reference to body member 102, engagement members 104, at least one opening 106, compression slot 108, and aperture 110, which will not be described again here for brevity sake. The engagement portions 984 may extend parallel to each other as they extend away from the body member 942. The engagement members 996 may extend perpendicular to the body member 942. The engagement members 996 may assist in holding the engagement portions 984 in the holes formed in a bone segment. The engagement members 996 may have, for example, ridges, barbs, spikes, and teeth-like or tine-like structures located along the perpendicular length of the engagement portions 984. The aperture 990 of the implant 980 may also include threads 992 or another similar locking feature. As shown in FIG. 47D, the aperture 990 may be tapered, for example, from the top surface to the bottom surface of the body member 982. The body member 982 may have, for example, a generally rectangular or oval shape with indents or grooves 994 on each side of the body member 982 and positioned between the compression slot 988 and the aperture 990. The implants 980 may come in a variety of sizes to correspond to the different size metatarsal bones in people Another implant system including implant 980 and fastener 1000 are shown in FIGS. 48A-48D. The implant 980 is of the type described above with reference to FIGS. 47A-47D, which will not be described again here for brevity sake. The fastener 1000 may be, for example, a bone screw or the like to secure the implant 980 to at least one bone. The fastener 100 may include a head 1002 with threads 1004 and a shaft 1006 with threads 1008. The threads 1004 and threads 1008 may be, for example, the same threads or different threads. The head 1002 may also include an opening 1012 for receiving an instrument, such as, a driver, for inserting the fastener 1000 into the patient's bone. The fastener 1000 may also include a tip 1010 at the end of the shaft 1006 opposite the head 1002.

The fastener 1000 may be, for example, a locking screw or non-locking screw. The fastener 1000 may be inserted through aperture 990 after a first fastener (not shown) has been inserted into the compression slot 988 and secured to the patient's bone. The threads 1008 of the shaft 1006 may pass through the aperture 990 without engaging the threads 992 in the aperture 990. As the head 1002 reaches the aperture 990 of the implant 980, the threads 1004 of the head 1002 engage the threads 992 of the aperture 990. The fastener 1000 may be inserted into the aperture 990 until the threads 1004 of the head 1002 cannot be threaded any further into the threads 992 of the aperture 990 locking the fastener 1000 into the implant 980.

Figure 49:
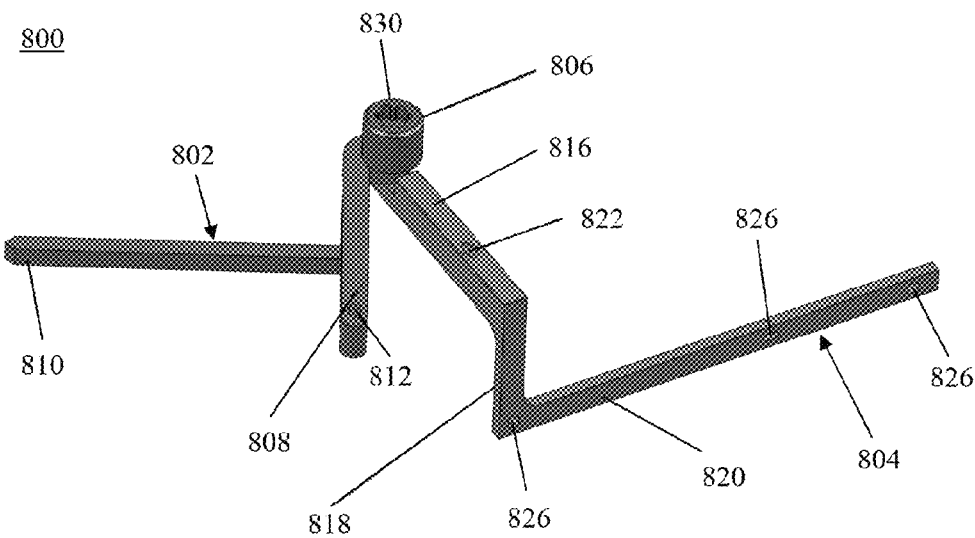
FIG. 49 is a perspective view of one embodiment bone cutting guide, in accordance with an aspect of the present invention.
Figure 50:
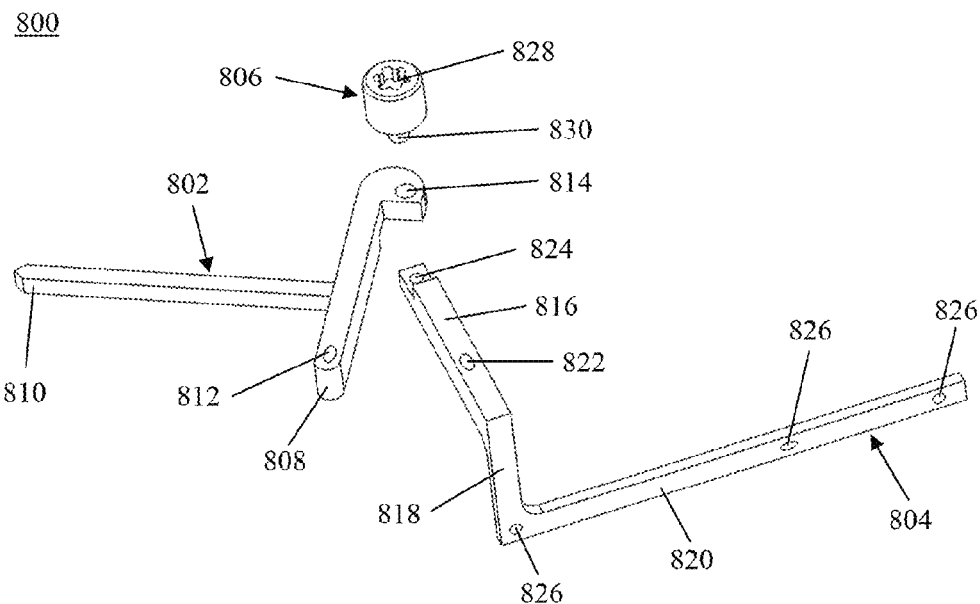
FIG. 50 is an exploded perspective view of the bone cutting guide of FIG. 49, in accordance with an aspect of the present invention.

FIGS. 49-50 and 52-55 show yet another embodiment of a cutting guide 800, including a first portion 802 and a second portion 804. The first portion 802 may be coupled, for example, hingedly coupled, to the second portion 804 by a locking screw 806. The first portion 802 may include a cutting or reference surface 808 and an alignment member 810. The cutting surface 808 may include a first opening 812 at a first end for receiving a fixation mechanism, for example, a k-wire (not shown) and a second opening 814 at a second end configured to receive the locking screw 806. As shown in FIGS. 49 and 50, the second portion 804 may include a first member 816, a first cutting or reference surface 818, and a second cutting or reference surface 820. The first cutting surface 818 and second cutting surface 820 may be, for example, relatively perpendicular. The first member 816 may include a first opening 822 configured to receive a fixation mechanism, for example, a k-wire (not shown), and a second opening 824 configured to receive the locking screw 806. The second cutting surface 820 may also include at least one opening 826 configured to receive a fixation mechanism, for example, a k-wire (not shown) to secure the guide 800 to a bone for cutting the bone.

The locking screw 806, as seen in FIG. 50, may include a tool opening 828 on a first end and a locking protrusion 830 on a second end opposite the first end. The tool opening 828 may be, for example, a hexagon, square, or other multi-lobed configuration allowing a tool to engage the opening 828 for insertion and tightening. The locking protrusion 830 may be configured, for example, with threads, to engage the openings 814, 824 which may also be, for example, threaded with corresponding threads to the locking protrusion 830. Other known locking screws 806 known by one skilled in the art are also contemplated.

Figure 51:
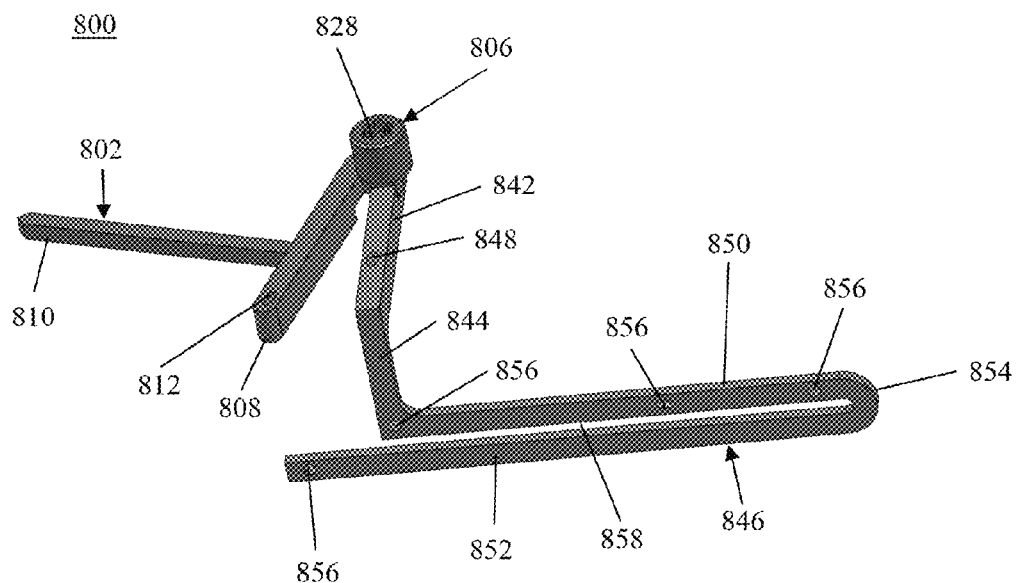
FIG. 51 is a perspective view of another embodiment bone cutting guide, in accordance with an aspect of the present invention.
Figure 56:
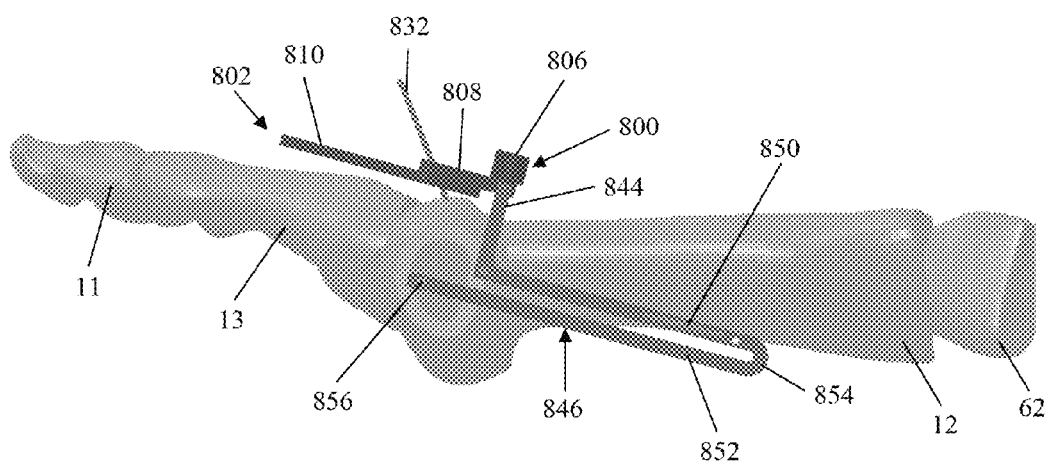
FIG. 56 is a side view of the bone cutting guide of FIG. 51 aligned on a patient's toe, in accordance with an aspect of the present invention.
Figure 57:
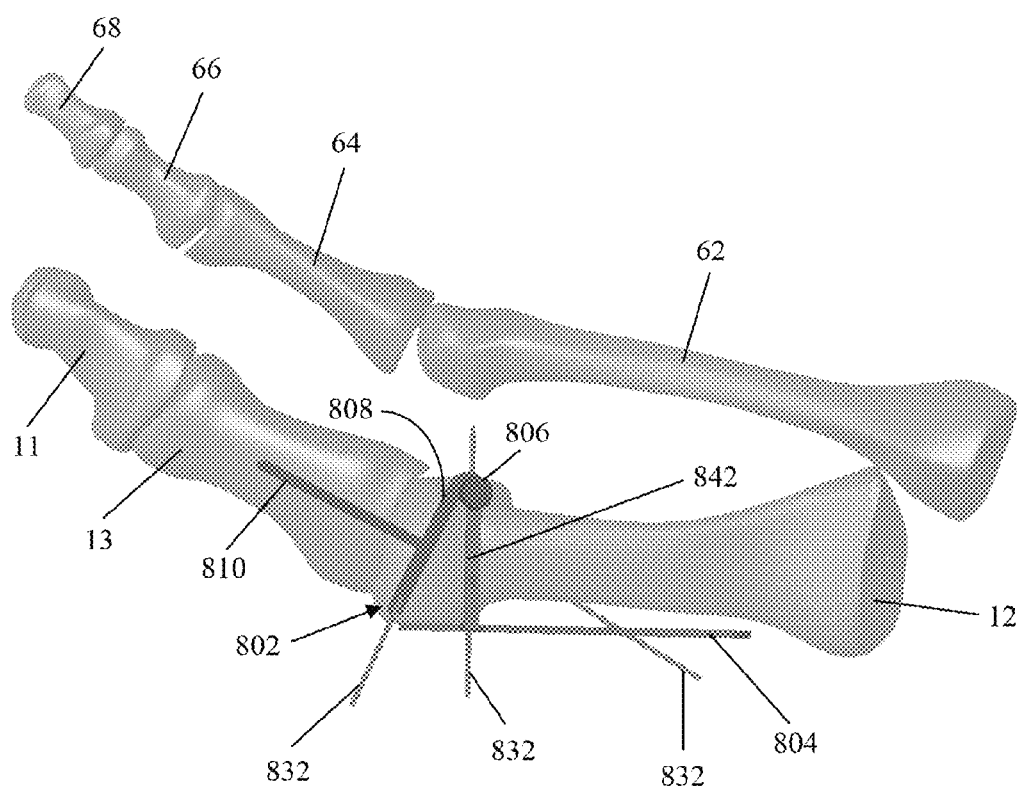
FIG. 57 is a top view of the bone cutting guide of FIG. 51 aligned on a patient's toe, in accordance with an aspect of the present invention.

Another embodiment of guide 800 is shown in FIGS. 51 and 56-57. The guide 800 shown in FIGS. 51, 56, and 57 includes the first portion 802 and a second portion 840 in place of the second portion 804 as described above with reference to FIGS. 49 and 50. The first portion 802 may be coupled, for example, hingedly coupled, to the second portion 840 by locking screw 806. The first portion 802 and locking screw 806 are of the type described above with reference to FIGS. 49 and 50 and for brevity sake will not be described again here. The second portion 840 may include a first member 842, a first cutting or reference surface 844, and a second cutting or reference surface 846. The first member 842 may include a first opening 848 configured to receive a fixation mechanism, for example, a k-wire (not shown), and a second opening (not shown), of the type described above with reference to opening 824 and configured to receive the locking screw 806. The second cutting surface 846 may include a first arm 850, a second arm 852, and an end member 854 connecting the first arm 850 and the second arm 852. The first cutting surface 844 and second cutting surface 846 may be, for example, relatively perpendicular. The second cutting surface 846 may also include at least one opening 856 configured to receive a fixation mechanism, for example, a k-wire (not shown) to secure the guide 800 to a bone for cutting. In addition, the second cutting surface 846 may include a reference surface 858 configured for the cutting tool to be inserted into to cut the bone. The openings 812, 822, 826, 848, and 856 may be, for example, angled or straight through the first portion 802 and second portions 804, 840 for insertion into the patient's bone to hold the guide 800 in place while the bone is cut.

Figure 52:
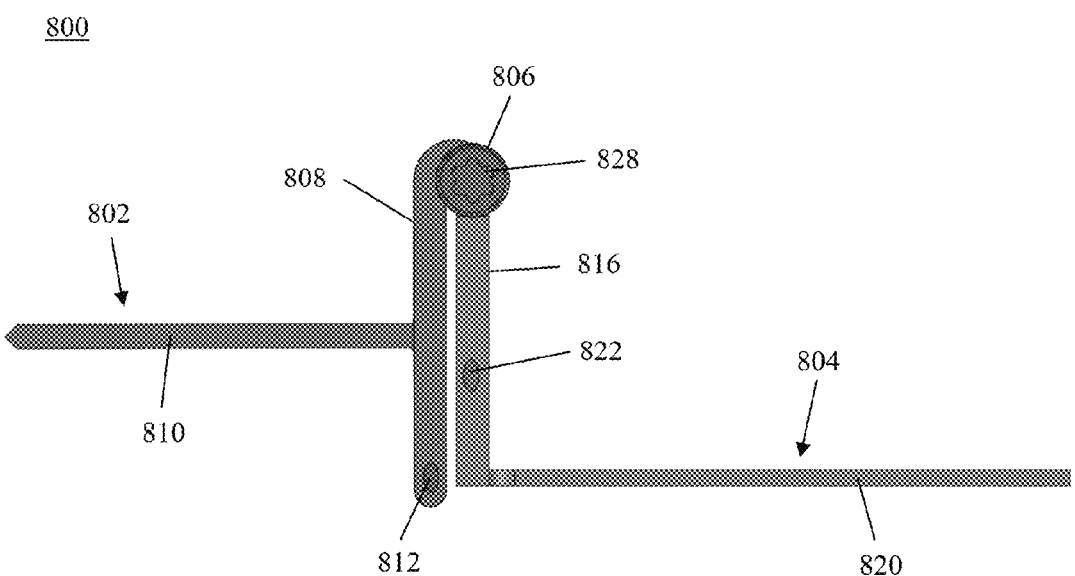
FIG. 52 is a top view of the bone cutting guide of FIG. 49 positioned at a cutting angle of about zero degrees, in accordance with an aspect of the present invention.
Figure 53:
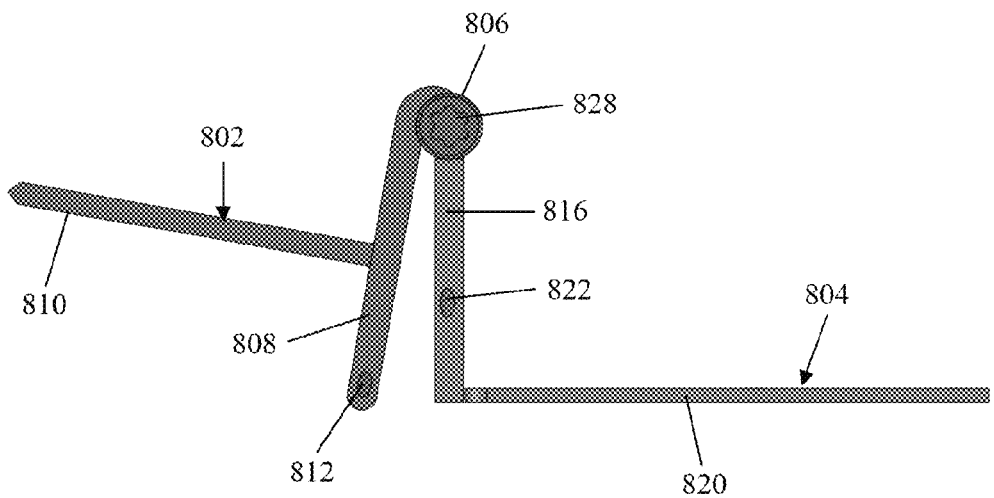
FIG. 53 is a top view of the bone cutting guide of FIG. 49 positioned at a cutting angle of about 10 degrees, in accordance with an aspect of the present invention.
Figure 54:
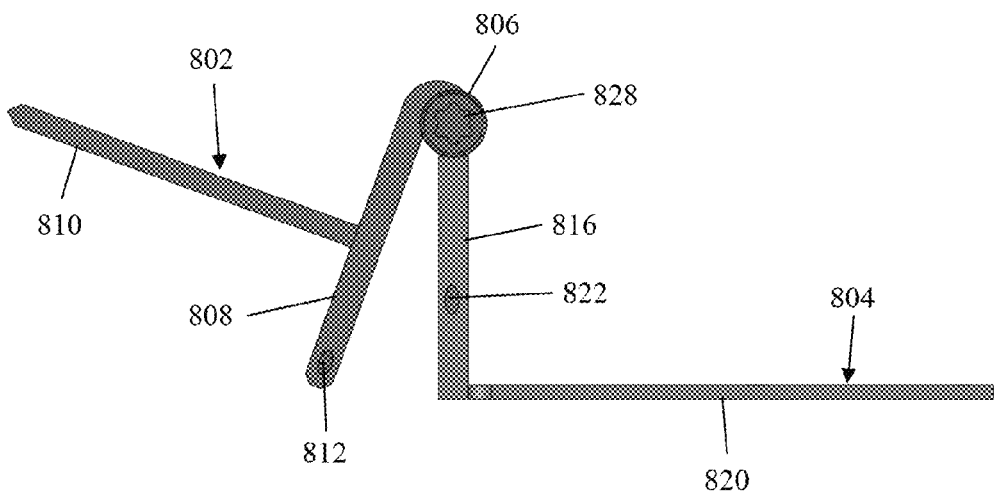
FIG. 54 is a top view of the bone cutting guide of FIG. 49 positioned at a cutting angle of about twenty degrees, in accordance with an aspect of the present invention.
Figure 55:
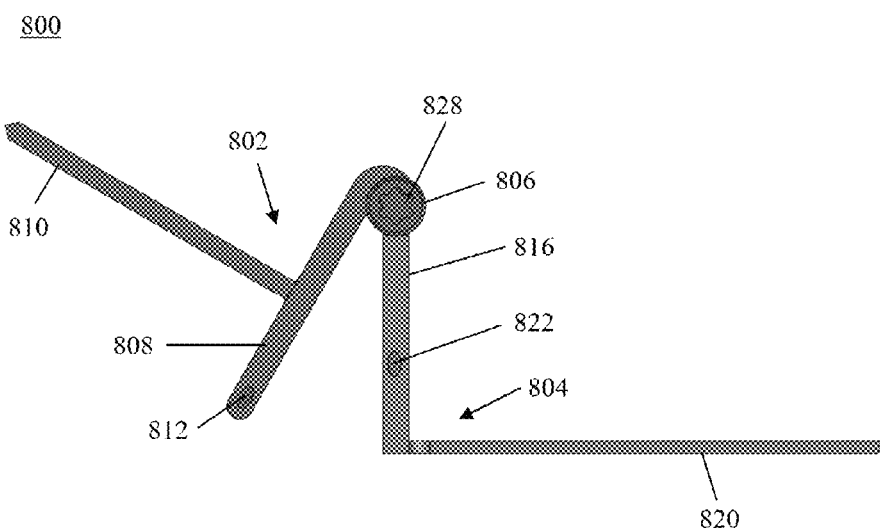
FIG. 55 is a top view of the bone cutting guide of FIG. 49 positioned at a cutting angle of about thirty degrees, in accordance with an aspect of the present invention.

As shown in FIGS. 52-55, the guide 800 may be adjusted to various degree cutting angles. The guide 800 may be set at specific angles in order to make the cuts necessary to correct specific angular deformities. The guide 800 may have a cutting angle ranging from, for example, about 0° to about 45°, and more preferably from about 0° to about 30°. A cutting angle of about 0° is shown in FIG. 52, a cutting angle of about 10° is shown in FIG. 53, a cutting angle of about 20° is shown in FIG. 54 and a cutting angle of about 30° is shown in FIG. 55.

Referring now to FIGS. 56 and 57, the guide 800 may be secured to the metatarsal bone 12 after the protruding portion of bone is removed, for example, after a bunionectomy is performed. The guide 800 may be aligned on the patient's metatarsal bone 12 by aligning the alignment member 810 along the proximal phalanx 13 and aligning the second portion 804, 840 with the resected bone surface. During alignment of the guide 800 on the bone, the locking screw 806 may be loosened to allow for adjustment of the cutting angle. Once the position and desired cutting angle are selected, the locking screw 806 may be tightened to secure the guide 800 in the desired position. Next the guide 800 may be secured to the bone using temporary fasteners 832, for example, k-wires. After fastening the guide 800 to the metatarsal bone 12, one or more of the reference surfaces 818, 820, 844, 846 and reference surface 856 may be used to cut the metatarsal bone 12 to correct the deformity. Once the cuts are made the k-wires 832 may be removed from the guide 800 and the guide 800 may be removed from the patient's foot to allow for the bones to be realigned and an implant, for example, implant 100 to be attached to the patient's bones, as described above.

It should be noted that the guides 20, 70, 200, 300, 400, 500 and 800 may be used with other bones within the body for osteotomies.

Figure 58:
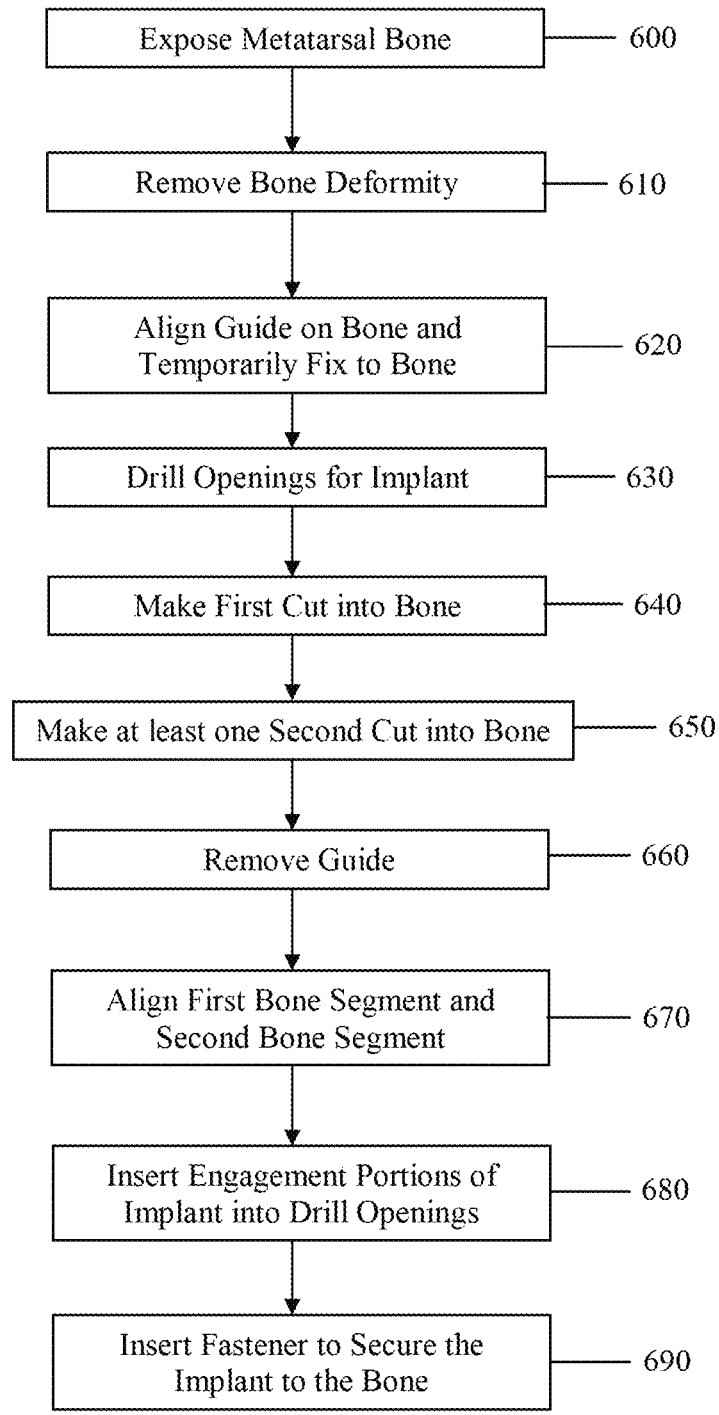
FIG. 58 depicts one embodiment of a surgical method for correcting a hallux valgus deformity, in accordance with an aspect of the present invention.
Figure 59:
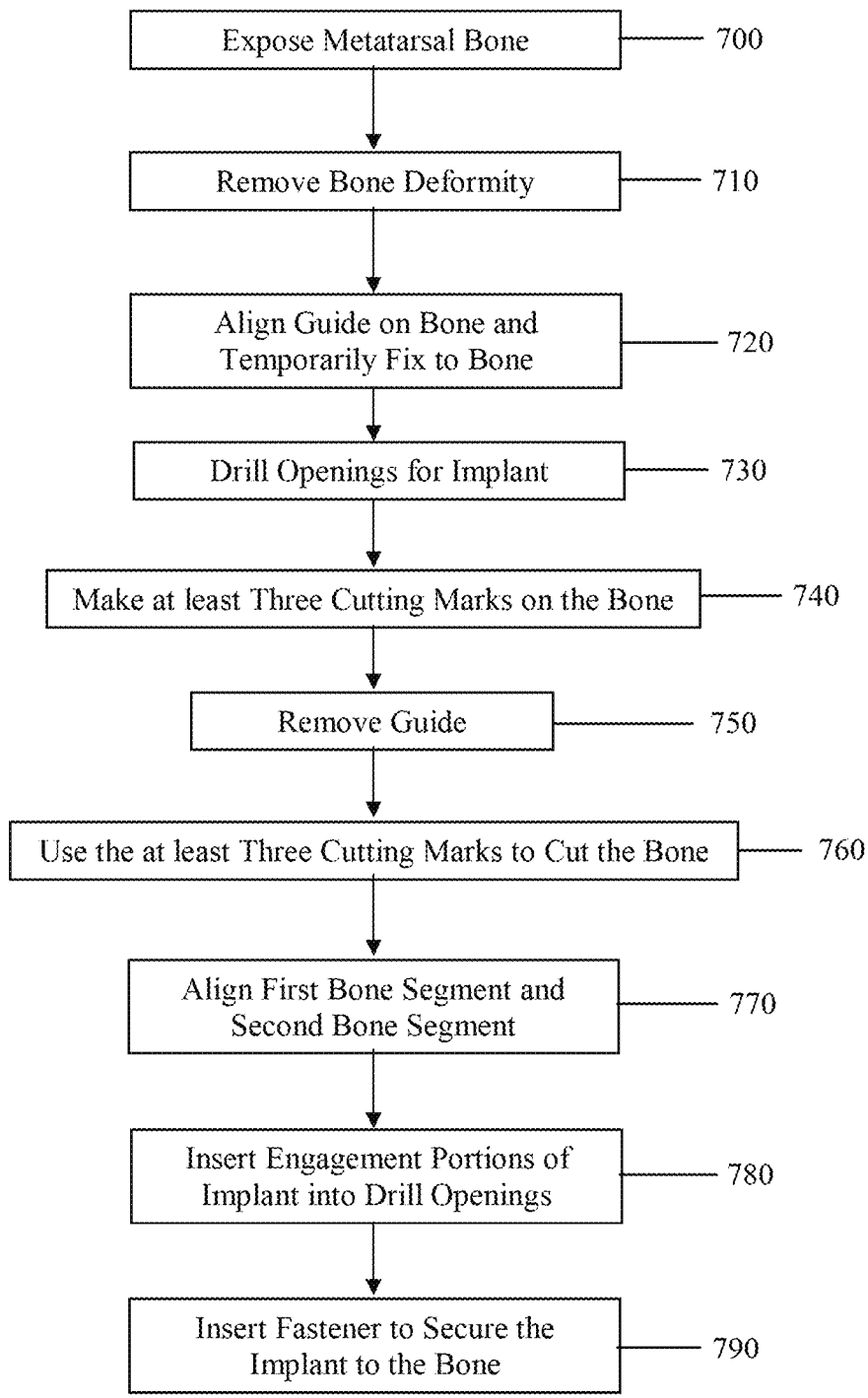
FIG. 59 depicts another embodiment of a surgical method for correcting a hallux valgus deformity, in accordance with an aspect of the present invention.

Referring now to FIGS. 58 and 59, surgical methods for using the guides 20, 200, 300, 400, and 500 with implant 100 to correct a hallux valgus deformity are shown. The surgical method shown in FIG. 58 includes exposing a bone including a bone deformity 600. Then the medial eminence, bone deformity, or bunion is removed 610 by, for example, an exostectomy procedure. Next, a guide, for example, guide 20, 300, 400, is aligned on the bone over the area where the bunion was removed and temporarily fixed to the bone 620. Then openings may be drilled for an implant 630, for example, implant 100. An osteotomy may then be performed by making a first cut into the bone using a reference surface in the guide 640. At least one second cut may be made into the bone using at least one additional reference surface in the guide 650. After the openings are drilled and the osteotomy is completed, the guide may be removed from the bone 660. Next, the two portions of bone created by the osteotomy may be aligned and compressed 670. Once a desired alignment and compression is achieved an implant may be inserted into the openings 680. At least one fastener may then be inserted to secure the implant to the bone 690. As the at least one fastener is inserted into the bone the implant may also allow for additional compression to occur from the force of the fastener being screwed into the bone. The patient's incision may then be closed.

The surgical method shown in FIG. 59 includes exposing a bone including a bone deformity 700. Next, the bone deformity, bunion, or medial eminence may be removed 710, for example, by an exostectomy procedure. Then a guide, for example, guide 200 or 500 may be aligned on the bone surface over the area where the bunion was removed and temporarily fixed to the bone 720. Once the guide is fixed to the bone, openings may be drilled for the implant 730, for example, implant 100. Next, at least three cutting marks may be made on the bone using the guide 740. The cutting marks may be, for example, drilled openings or a mark on the bone using a marking tool. After the cutting marks are made on the bone, the temporary fixation devices may be removed and the guide may be removed from the bone 750. The cutting marks may then be used to perform an osteotomy by cutting the bone along lines created by the cutting marks 760. The two segments of bone created by cutting the bone may then be aligned and compressed 770. An implant may then be inserted into the openings and aligned along the longitudinal axis of the bone 780. At least one fastener may then be used to secure the implant to the bone in the selected position 790. Once the implant is attached to the bone, the patient may be closed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A resection guide, comprising: a plate with a first end opposite a second end and a medial portion extending therebetween; at least one opening in the first end of the plate; at least one hole positioned along a longitudinal axis of the plate near the at least one opening; a first notch on a first side of the medial portion; a second notch on a second side of the medial portion; at least one aperture positioned in the medial portion of the plate and extending from a top surface to a bottom surface of the plate; a first cutout positioned at the first end of the plate; a first tab positioned at the first end of the plate, wherein the first tab is positioned within the first cutout; a second cutout positioned at the second end of the plate; and a second tab positioned at the second end of the plate, wherein the second tab is positioned within the second cutout.

2. The resection guide of claim 1, wherein the at least one aperture is positioned along the longitudinal axis of the plate between the first and second cutouts and the second end.

3. The resection guide of claim 2, wherein the at least one opening is two openings.

4. The resection guide of claim 3, wherein the first tab is positioned between the two openings.

5. The resection guide of claim 3, wherein the at least one opening is at least one screw sleeve.

6. The resection guide of claim 5, wherein the at least one screw sleeve extends out from the top surface of the plate.

7. The resection guide of claim 2 wherein the at least one hole is relatively centered between the two openings of the at least two openings.

8. The resection guide of claim 1, further comprising:
at least one screw sleeve comprising:
a body with an exterior circumference; and
an extension protruding out from a bottom surface of the body and having an exterior circumference that is smaller than the exterior circumference of the body;
wherein the extension of the at least one sleeve is sized to engage the at least one opening in the first end of the plate.

9. The resection guide of claim 1, further comprising:
at least one alignment line positioned in the medial portion.

* * * * *